United States Patent
Morita et al.

(10) Patent No.: US 10,781,325 B2
(45) Date of Patent: Sep. 22, 2020

(54) CURABLE COMPOSITION, CURABLE INK, ACCOMMODATING CONTAINER, IMAGE FORMING DEVICE, IMAGE FORMING METHOD, CURED MATTER, AND ACRYLAMIDE COMPOUND

(71) Applicants: Mitsunobu Morita, Shizuoka (JP); Soh Noguchi, Kanagawa (JP); Takashi Okada, Kanagawa (JP); Kazukiyo Nagai, Shizuoka (JP); Yuusuke Koizuka, Kanagawa (JP); Tomoyuki Shimada, Shizuoka (JP)

(72) Inventors: Mitsunobu Morita, Shizuoka (JP); Soh Noguchi, Kanagawa (JP); Takashi Okada, Kanagawa (JP); Kazukiyo Nagai, Shizuoka (JP); Yuusuke Koizuka, Kanagawa (JP); Tomoyuki Shimada, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 66 days.

(21) Appl. No.: 15/808,101

(22) Filed: Nov. 9, 2017

(65) Prior Publication Data
US 2018/0127607 A1    May 10, 2018

(30) Foreign Application Priority Data

Nov. 9, 2016 (JP) .................................. 2016-219148
Sep. 13, 2017 (JP) .................................. 2017-175587

(51) Int. Cl.
C09D 11/101    (2014.01)
C07C 233/00    (2006.01)
(Continued)

(52) U.S. Cl.
CPC .......... *C09D 11/101* (2013.01); *C07C 233/00* (2013.01); *C07C 233/20* (2013.01); *C09D 4/00* (2013.01); *C09D 11/30* (2013.01)

(58) Field of Classification Search
CPC .................................................. C09D 11/101
(Continued)

(56) References Cited

U.S. PATENT DOCUMENTS

2009/0286435 A1    11/2009 Badyal et al.
2014/0120326 A1    5/2014 Morita et al.
(Continued)

FOREIGN PATENT DOCUMENTS

CN    101516496 A    8/2009
CN    104231744 A    12/2014
(Continued)

OTHER PUBLICATIONS

Extended European Search Report dated Jan. 25. 2018 in Patent Application No. 17200644.7, 7 pages.
(Continued)

*Primary Examiner* — Duc Truong
(74) *Attorney, Agent, or Firm* — Oblon, McClelland, Maier & Neustadt, L.L.P.

(57) ABSTRACT

A curable composition includes an acrylamide compound represented by the following Chemical formula 1:

Chemical formula 2

(Continued)

where $R_1$ represents an alkyl group having 1 to 6 carbon atoms, X represents an alkylene group having 1 to 6 carbon atoms, and Y represents the following Chemical formula 2 or the following Chemical formula 3,

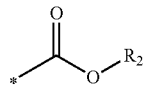

Chemical formula 3 where $R_2$ represents an alkyl group having 1 to 10 carbon atoms and * represents a bond site with X,

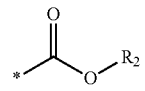

Chemical formula 3 where $R_2$ represents an alkyl group having 1 to 10 carbon atoms and * represents a bond site with X.

6 Claims, 3 Drawing Sheets

(51) Int. Cl.
    *C07C 233/20*      (2006.01)
    *C09D 4/00*      (2006.01)
    *C09D 11/30*      (2014.01)

(58) Field of Classification Search
    USPC ........................................................ 528/310
    See application file for complete search history.

(56) References Cited

U.S. PATENT DOCUMENTS

| 2014/0363634 A1 | 12/2014 | Morita et al. |
| 2017/0137644 A1 | 5/2017 | Morita et al. |

FOREIGN PATENT DOCUMENTS

| EP | 2 810 996 A2 | 12/2014 |
| JP | 2008-248251 | 10/2008 |
| JP | 2014-101490 | 6/2014 |
| JP | 2015-013980 | 1/2015 |
| WO | WO2008/012064 | 1/2008 |

OTHER PUBLICATIONS

Manat Renil, et al. "Synthesis and Application of a PEGA Polymeric Support for High Capacity Continuous Flow Solid-Phase Peptide Synthesis", Tetrahedron Letters, vol. 36, No. 26, XP004027835, 1995, pp. 4647-4650.
Office Action in corresponding Chinese Application No. 201711058493.4, dated Jul. 1, 2020.
W. Schofield, et al., "Direct Write Tethered Protein Arrays", Journal of Materials Chemistry, 2011, 21, pp. 14072-14078.
E. Savariar, et al., "Supramolecular Assemblies from Amphiphilic Homopolymers: Testing the Score", Department Chemistry, University of Massachusetts, Amherst, Massachusetts 01003, 2006, pp. S1-S20.
T. Wood, et al., "Atomized Spray Plasma Deposition of Structurally Well-Defined Bioactive Coatings", Plasma Chem. Plasma Process, 2014, 34, pp. 1019-1031.

CURABLE COMPOSITION, CURABLE INK, ACCOMMODATING CONTAINER, IMAGE FORMING DEVICE, IMAGE FORMING METHOD, CURED MATTER, AND ACRYLAMIDE COMPOUND

CROSS-REFERENCE TO RELATED APPLICATIONS

This patent application is based on and claims priority pursuant to 35 U.S.C. § 119 to Japanese Patent Application Nos. 2016-219148 and 2017-175587, filed on Nov. 9, 2016, and Sep. 13, 2017, respectively, in the Japan Patent Office, the entire disclosures of which are hereby incorporated by reference herein.

BACKGROUND

Technical Field

The present invention relates to a curable composition, a curable ink, an accommodating container, an image forming device for two-dimensional images or three-dimensional images, an image forming method for two-dimensional images or three-dimensional images, cured matter, and an acrylamide compound.

Description of the Related Art

Inkjet recording methods are known as methods of forming images on recording media, typically paper. This inkjet recording method has a high ink consumption efficiency and excellent resource saving property. Therefore, ink cost per unit of recording can be reduced.

Ink jet recording methods using curable ink have been appealing. For example, ink has been proposed which uses a tertiary acrylamide having an ester structure.

SUMMARY

According to the present invention, provided is an improved curable composition including:
an acrylamide compound represented by the following Chemical formula 1:

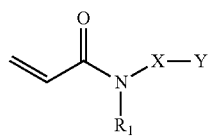

Chemical formula 1 where $R_1$ represents an alkyl group having 1 to 6 carbon atoms, X represents an alkylene group having 1 to 6 carbon atoms, and Y represents the following Chemical formula 2 or the following Chemical formula 3,

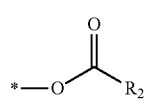

Chemical formula 2 where $R_2$ represents an alkyl group having 1 to 10 carbon atoms and * represents a bond site with X,

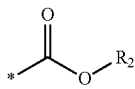

Chemical formula 3 where $R_2$ represents an alkyl group having 1 to 10 carbon atoms and * represents a bond site with X.

BRIEF DESCRIPTION OF THE SEVERAL VIEWS OF THE DRAWINGS

Various other objects, features and attendant advantages of the present invention will be more fully appreciated as the same becomes better understood from the detailed description when considered in connection with the accompanying drawings in which like reference characters designate like corresponding parts throughout and wherein.

Figure 1:
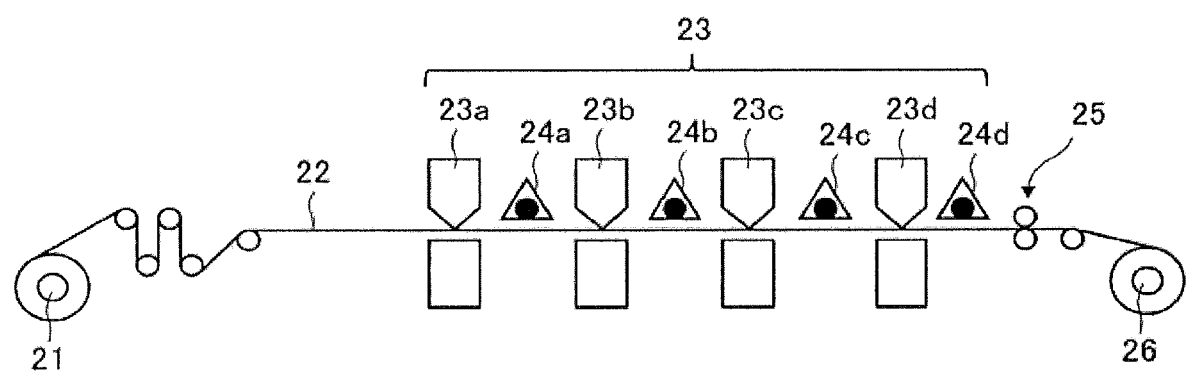
FIG. 1 is a schematic diagram illustrating an example of the image forming device according to an embodiment of the present disclosure.

The accompanying drawings are intended to depict example embodiments of the present invention and should not be interpreted to limit the scope thereof. The accompanying drawings are not to be considered as drawn to scale unless explicitly noted. Also, identical or similar reference numerals designate identical or similar components throughout the several views.

DESCRIPTION OF THE EMBODIMENTS

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

As used herein, the singular forms "a", "an", and "the" are intended to include the plural forms as well, unless the context clearly indicates otherwise.

Moreover, image forming, recording, printing, modeling, etc. in the present disclosure represent the same meaning, unless otherwise specified.

Curable Composition and Curable Compound

The curable composition of the present disclosure contains an acrylamide compound represented by the following Chemical formula 1, preferably other curable compounds, a polymerization initiator, an organic solvent, and optionally a coloring material, etc.

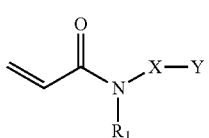

Chemical formula 1

In the Chemical formula 1, $R_1$ represents an alkyl group having 1 to 6 carbon atoms. X represents an alkylene group having 1 to 6 carbon atoms and Y represents the following Chemical formula 2 or the following Chemical formula 3.

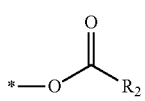

Chemical formula 2

In the Chemical formula 2, $R_2$ represents an alkyl group having 1 to 10 carbon atoms and * presents a bond site with X

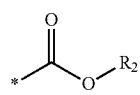

Chemical formula 3

In the Chemical formula 3, $R_2$ represents an alkyl group having 1 to 10 carbon atoms and * represents a bond site with X.

In addition, the curable compound of the present disclosure is the acrylamide compound represented by the following Curable formula 1.

Acrylamide Compound

The acrylamide compound is represented by the following Chemical formula 1.

In the Chemical formula 1, $R_1$ represents a straight chained or branch-chained alkyl group having 1 to 6 carbon atoms.

Specific examples of the alkyl group having 1 to 6 carbon atoms include, but are not limited to, methyl group, ethyl group, propyl group isopropyl group, n-butyl group, s-butyl group, isobutyl group, t-butyl group, pentyl group, neopentyl group, and hexyl group.

In the Chemical formula 1, X represents a straight chained or branch-chained alkylene group having 1 to 6 carbon atoms.

Specific examples of the alkylene group having 1 to 6 carbon atoms include, but are not limited to, methylene group, ethylene group, propylene group, and buthylene group.

In the Chemical formula 1, Y represents the following Chemical formula 2 or the following Chemical formula 3.

In the Chemical formula 2, $R_2$ represents a straight chained or branch-chained alkyl group having 1 to 10 carbon atoms.

Specific examples of the alkyl group having 1 to 10 carbon atoms include, but are not limited to, methyl group, ethyl group, propyl group, isopropyl group, n-butyl group, s-butyl group, isobutyl group, t-butyl group, pentyl group, neopentyl group, hexyl group, heptyl group, octyl group, nonyl group, and decyl group.

In the Chemical formula 2, * represents the bond site with X.

In the Chemical formula 3, $R_2$ represents a straight chained or branch-chained alkyl group having 1 to 10 carbon atoms.

Specific examples of the alkyl group having 1 to 10 carbon atoms include, but are not limited to, methyl group, ethyl group, propyl group, isopropyl group, n-butyl group, s-butyl group, isobutyl group, t-butyl group, pentyl group, neopentyl group, hexyl group, heptyl group, octyl group, nonyl group, and decyl group.

In the Chemical formula 3, * represents the bond site with X.

The acrylamide compound represented by the Chemical formula 1 includes an ester structure at a distal end of mono-functional tertiary acrylamide having no ring structure. In general, tertiary acrylamide having a low molecular weight is volatile, which produces odor peculiar to the monomers. This is uncomfortable when handling a curable composition containing these compounds.

For such a tertiary acrylamide compound having a low molecular weight, it is possible to reduce volatility and odor of the acrylamide compound by introduction of a functional group having a strong polarity thereinto or an increase of the molecular weight thereof. However, this accompanies an increase of viscosity, which significantly limits usability of the curable composition, in particular ink for inkjet.

The tertiary acrylamide compound represented by the Chemical formula 1 includes an ester structure at its distal end. This ester structure reduces volatility, thereby reducing odor.

In addition, curability is inferred to ameliorate due to mutual action between molecules due to the presence of the ester structure. Moreover, since the tertiary acrylamide compound having an ester structure does not form a strong hydrogen bond, an increase of viscosity is small so that viscosity is thought to be maintained low. As a consequence, the acrylamide compound represented by the Chemical formula 1 can be suitably used as a curable composition, in particular ink for inkjet ink.

In general, since acrylamide compounds are acute oral toxic, which arises concerns about safeness of curable compositions containing such compounds. Also, it has to be handled with care.

To the contrary, acute oral toxicity of the acrylamide compound having an ester structure of the present disclosure tends to decrease. Of these, when Y in the Chemical formula 1 is the Chemical formula 3, acute oral toxicity tends to be extremely low. Therefore, acute oral toxicity of the curable composition containing the acrylamide compound of the present disclosure is expected to be low, thereby enhancing safeness.

The acrylamide compound represented by the Chemical formula 1 has no specific limit and can be suitably selected to suit to a particular application. For example, the compound represented by the following Chemical Formula 4 is preferable.

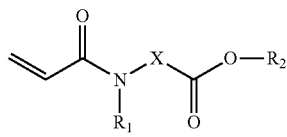

Chemical formula 4

In the Chemical formula 4, $R_1$ represents an alkyl group having 1 to 6 carbon atoms, X represents an alkylene group having 1 to 3 carbon atoms, and $R_2$ represents an alkyl group having 1 to 4 carbon atoms.

The alkyl group having 1 to 6 carbon atoms represented by $R_1$ can be straight-chained or branch-chained.

Specific examples include, but are not limited to, methyl group, ethyl group, propyl group, isopropyl group, n-butyl group, s-butyl group, isobutyl group, t-butyl group, pentyl group, neopentyl group, and hexyl group. Of these, R₁ is preferably an alkyl group having 1 to 3 carbon atoms more preferred are methyl group and ethyl group.

The alkylene group having 1 to 3 carbon atoms represented by X can be straight-chained or branch-chained.

Specific examples include, but are not limited to, methylene group, ethylene group, propylene group, methylmethylene group, and dimethylmethylene group. Of these, methylene group, methylmethylene group, and dimethylmethylene group are preferable and methylene group and methylmethylene group are more preferable.

The alkyl group having 1 to 4 carbon atoms represented by R₂ can be straight-chained or branch-chained.

Specific examples include, but are not limited so, methyl group, ethyl group, propyl group, isopropyl group, n-butyl group, s-butyl group, isobutyl group, and t-butyl group. Of these, methyl group, ethyl group, propyl group, isopropyl group, n-butyl group, and isobutyl group are preferable. More preferable is alkyl group when R₂ is an alkyl group having 1 to 3 carbon atoms.

Next, specific examples of the acrylamide compound represented by Chemical formula 1 include, but are not limited to, the following illustrated compounds of group a to group b.

Specific examples of the illustrated compounds of group a include, but are not limited to, the compounds of group a1 to group a6 below. These can be used alone or in combination.

Illustrated Compound of Group a1

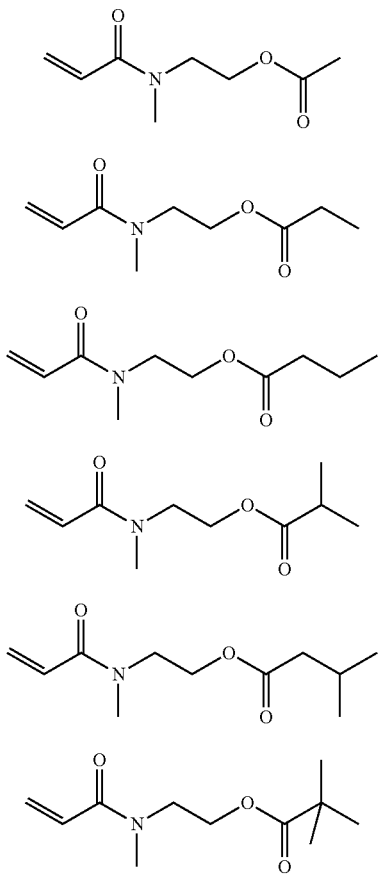

Illustrated Compound of Group a2

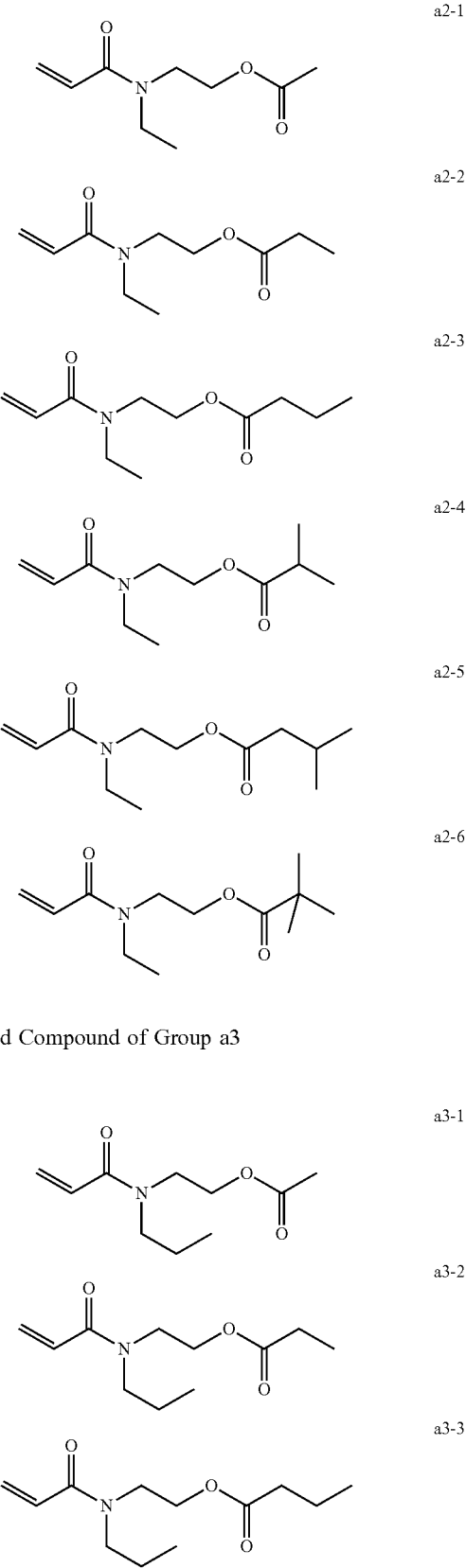

Illustrated Compound of Group a3

-continued
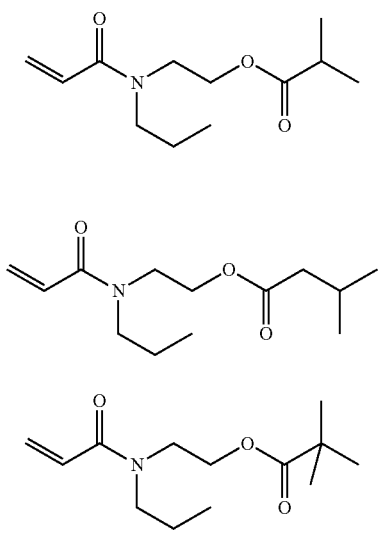
Illustrated Compound of Group a4
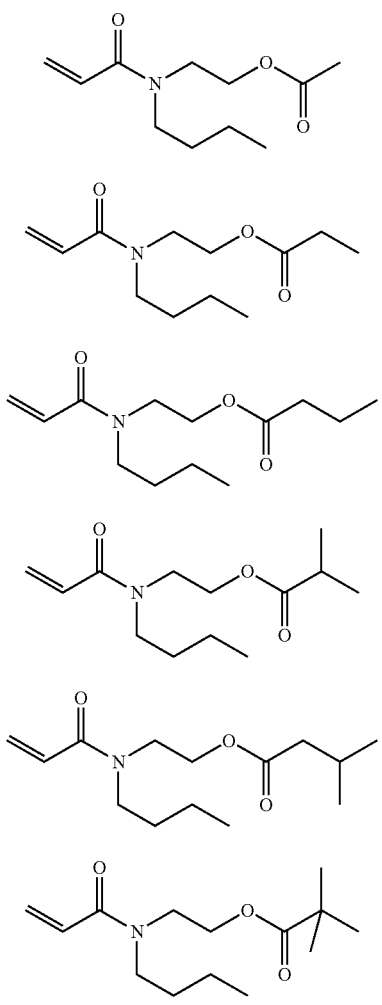
Illustrated Compound of Group a5
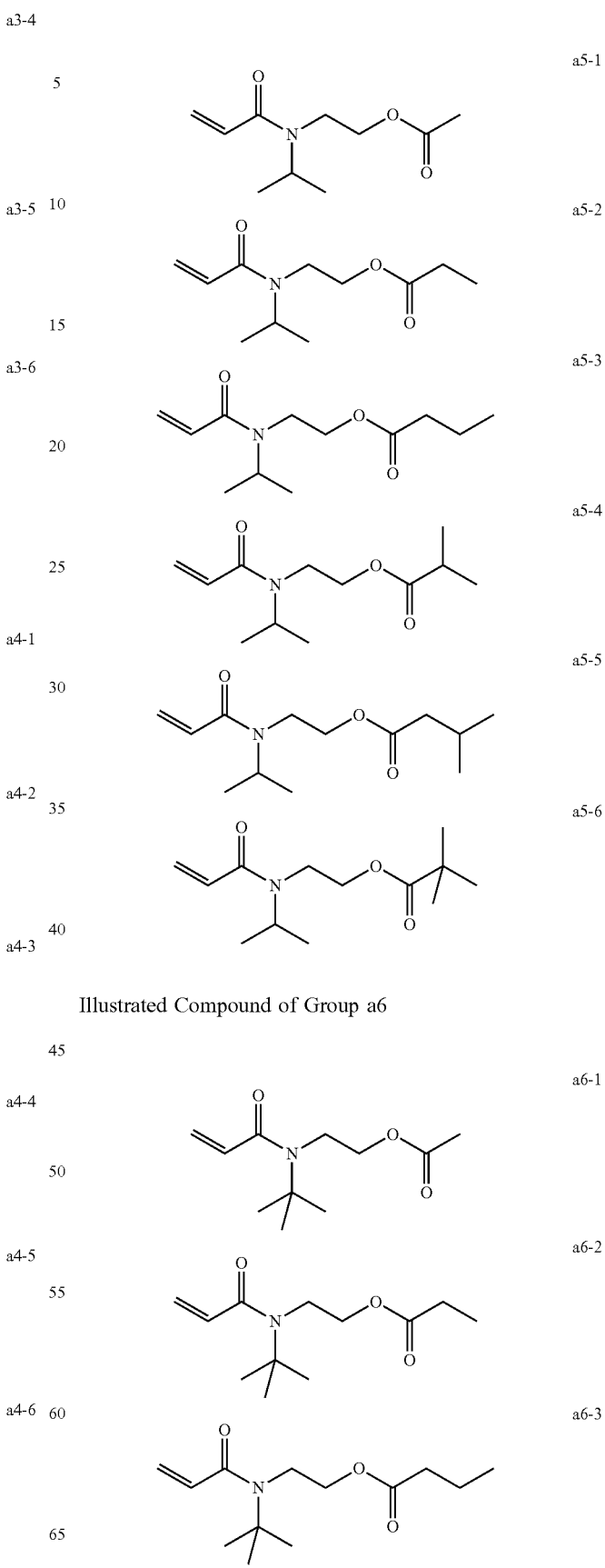
Illustrated Compound of Group a6 a6-4
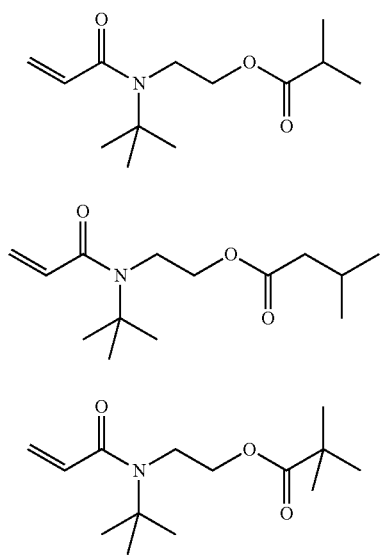
a6-5
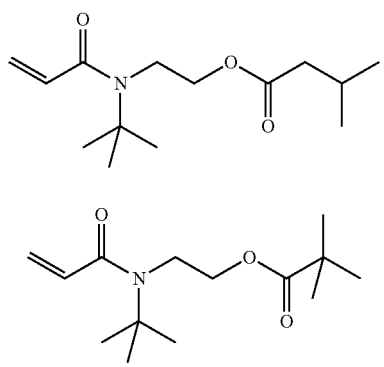
a6-6
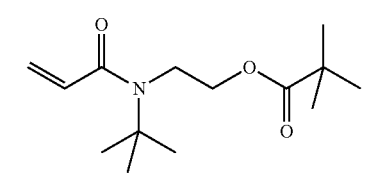
Specific examples of the illustrated compound of group b include, but are not limited to, the compounds of group b1 to group b6. These can be used alone or in combination.
Illustrated Compound b1 Group
b1-1
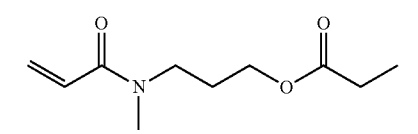
b1-2
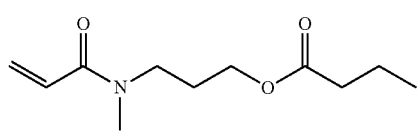
b1-3
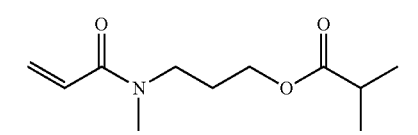
b1-4
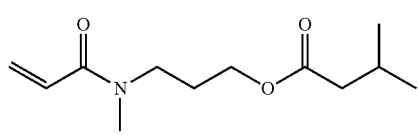
b1-5
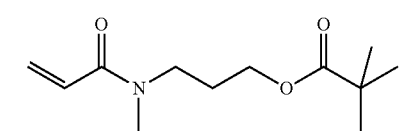
b1-6
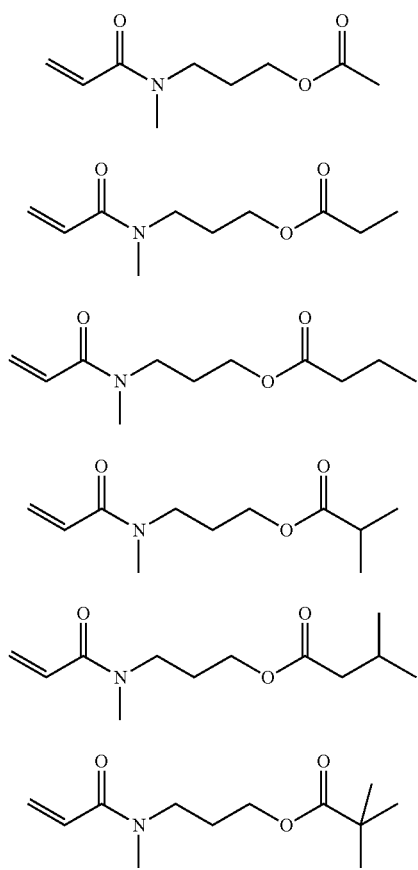
Illustrated Compound b2 Group
b2-1
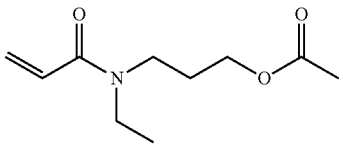
b2-2
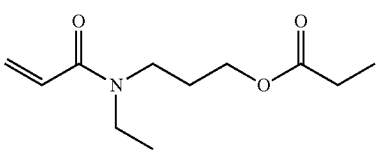
b2-3
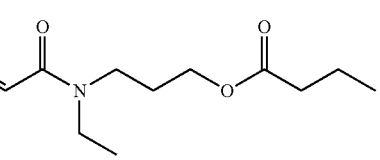
b2-4
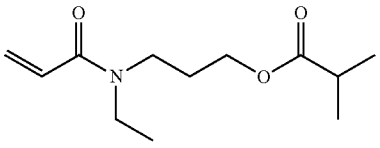
b2-5
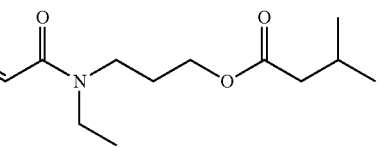
b2-6
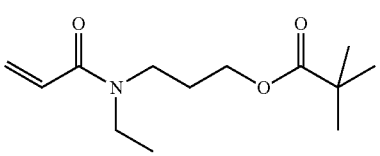
Illustrated Compound b3 Group
b3-1
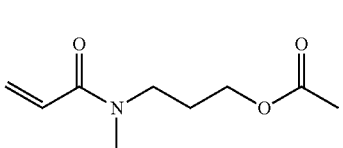
b3-2
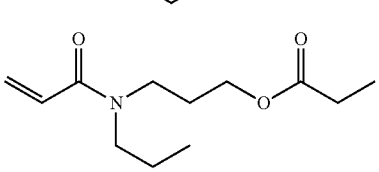
b3-3
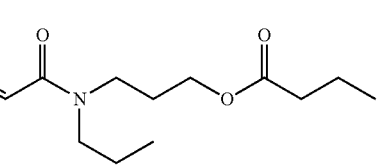

Illustrated Compound b4 Group
Illustrate Compound b5 Group
Illustrate Compound b6 Group
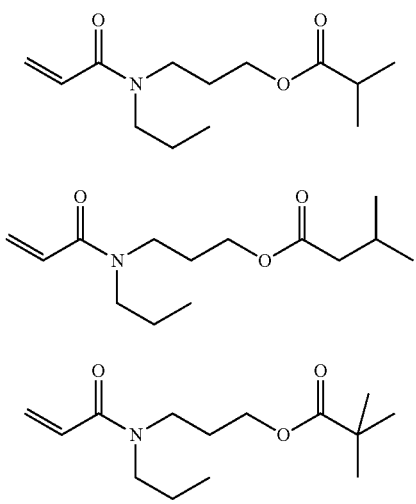
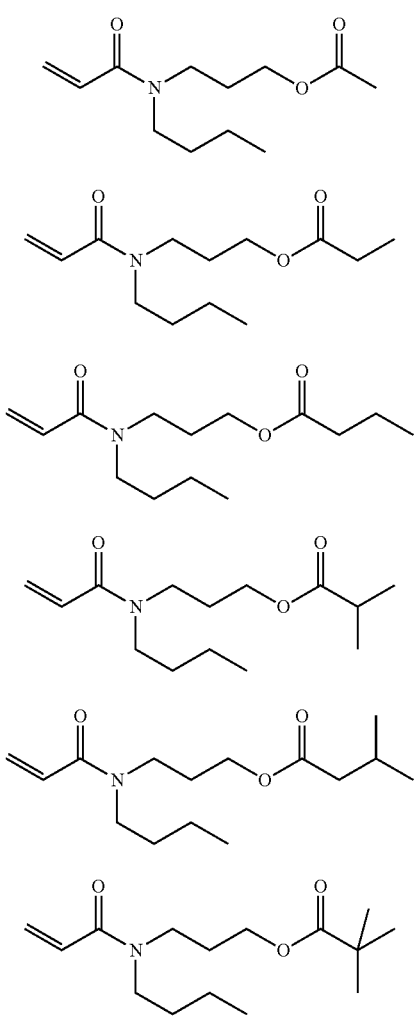
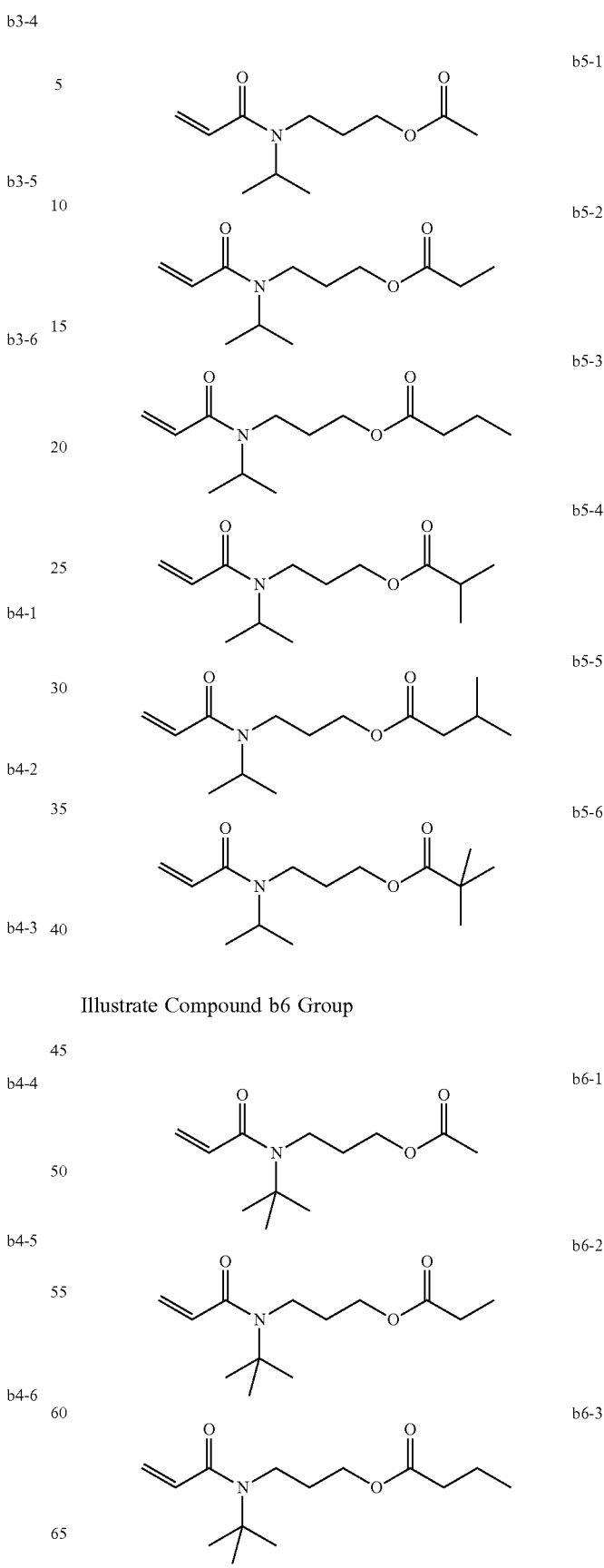

-continued
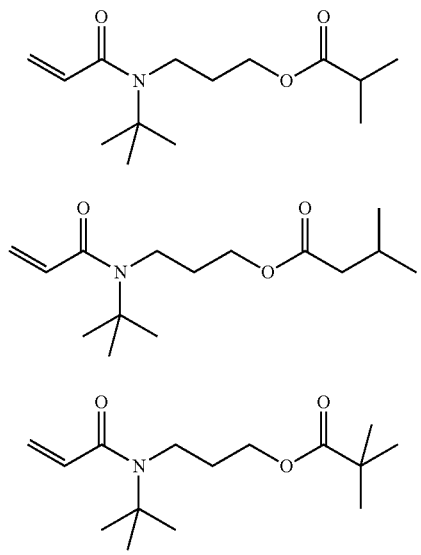
b6-4
b6-5
b6-6
Specific examples of the illustrated compound of group c include, but are not limited to the compounds of group c6 below. These can be used alone or in combination.
Illustrated Compound of Group c1
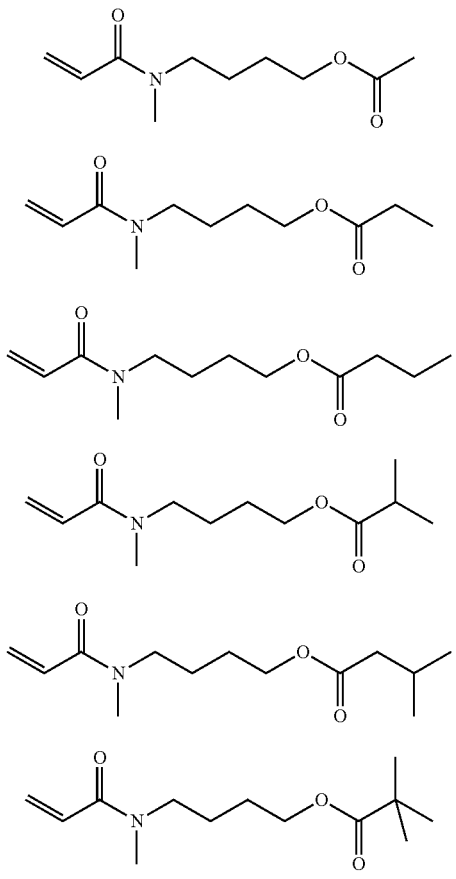
c1-1
c1-2
c1-3
c1-4
c1-5
c1-6
Illustrated Compound of Group c2
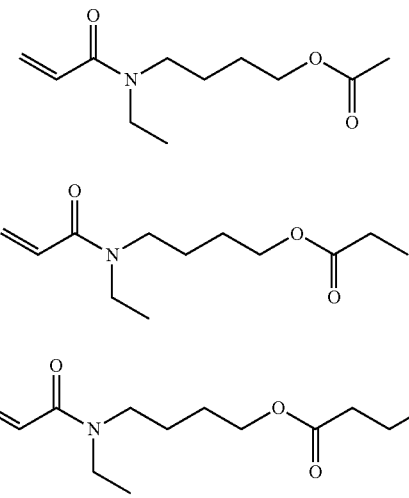
c2-1
c2-2
c2-3
c2-4
c2-5
c2-6
Illustrated Compound of Group c3
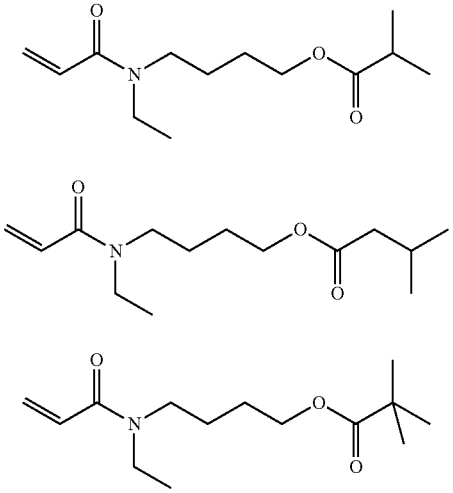
c3-1
c3-2
c3-3

-continued
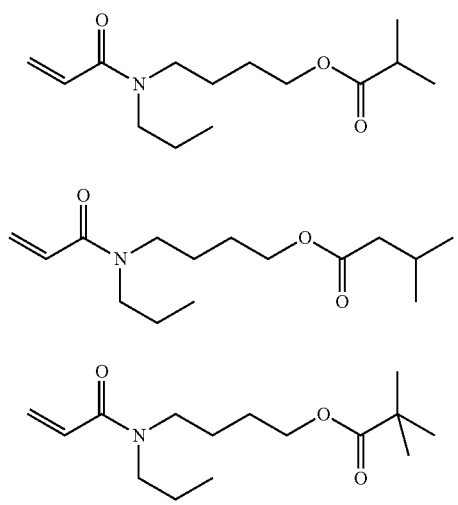
Illustrated Compound of Group c4
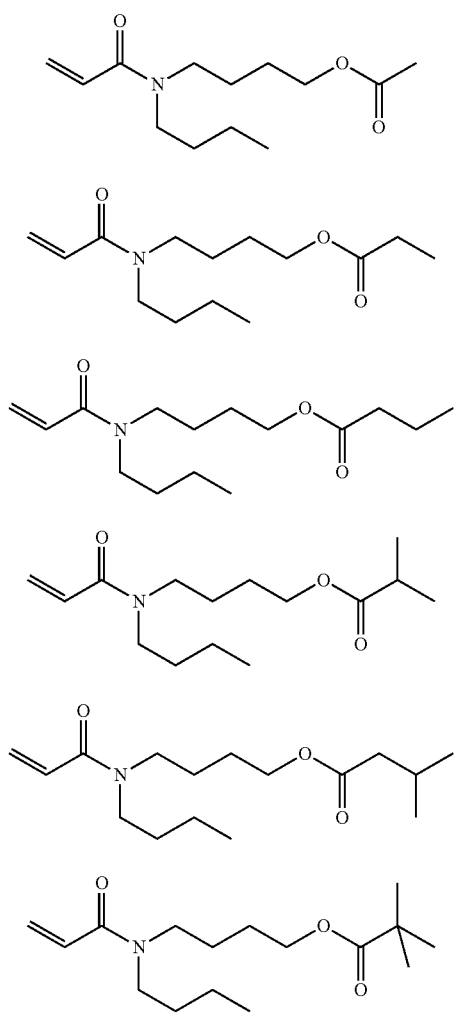
Illustrated Compound of Group c5
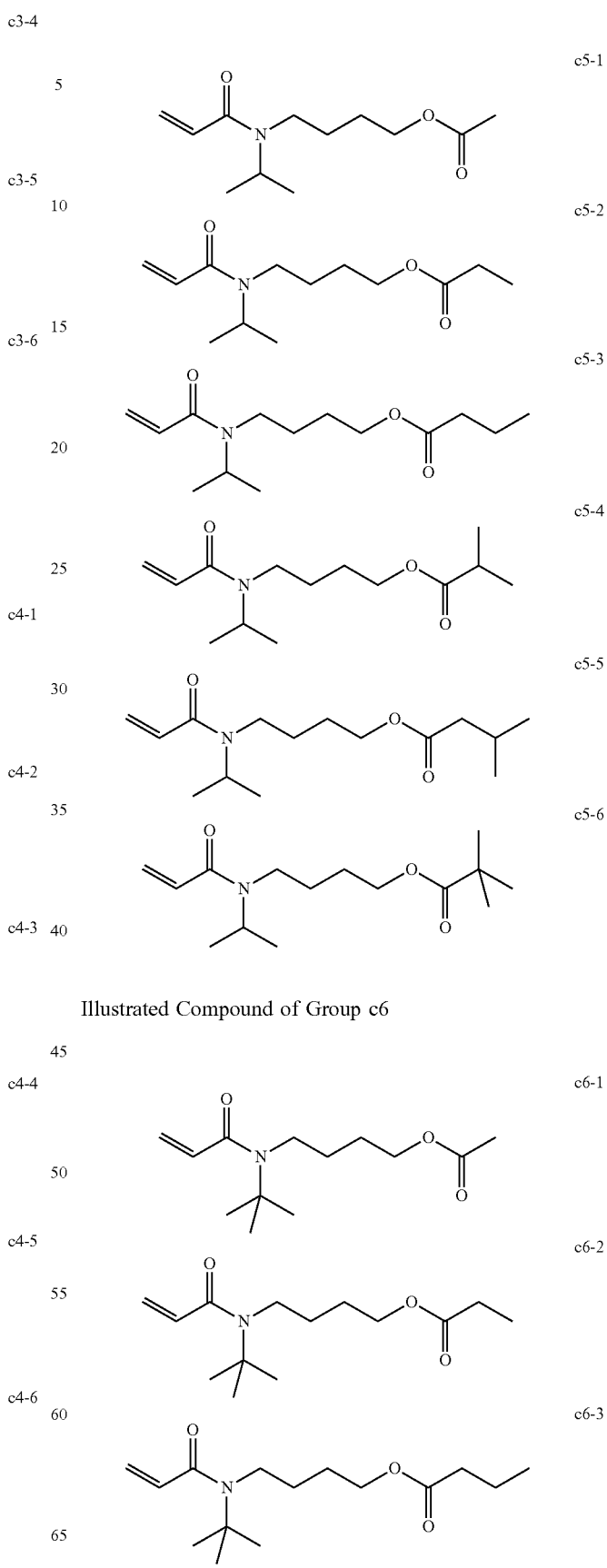
Illustrated Compound of Group c6
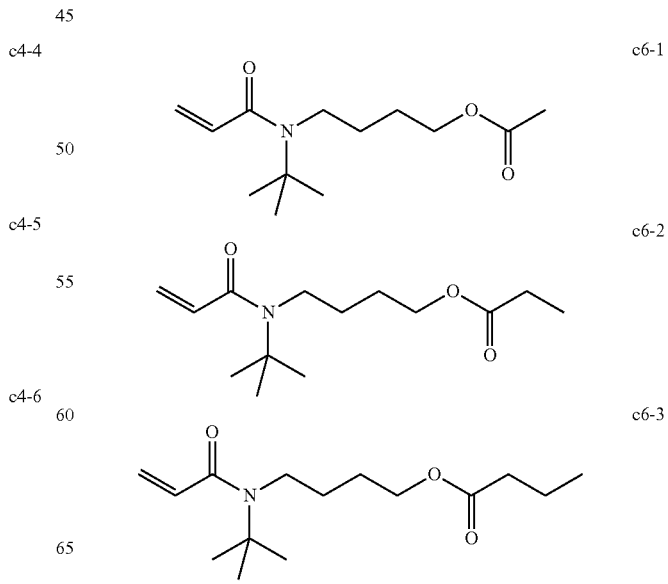

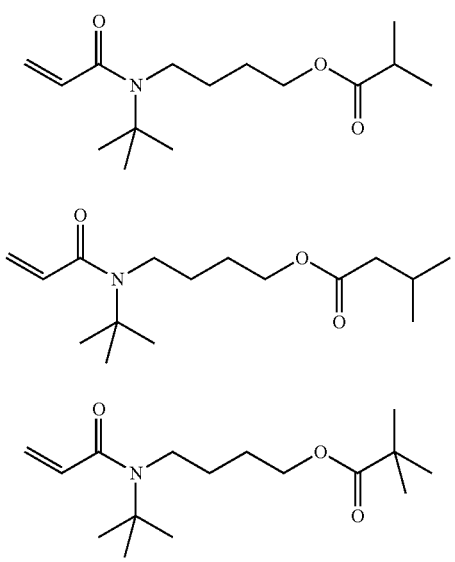
Specific examples of the illustrated compound group d include, but are not limited to, the compounds of group d1 to group d6 below. These can be used alone or in combination.
Illustrated Compound of Group d1
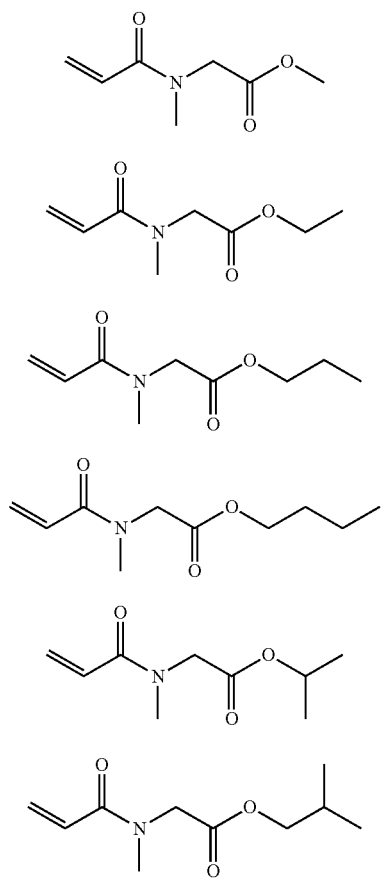
Illustrated Compound of Group d2
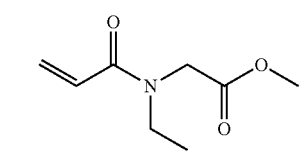
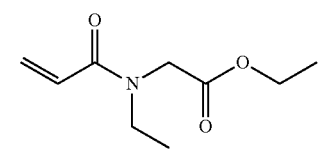
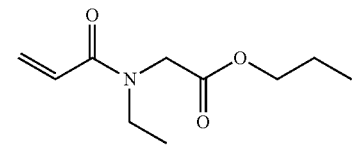
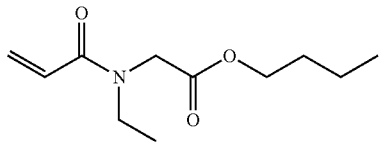
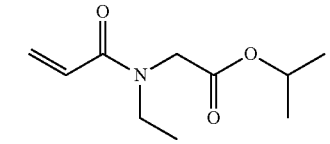
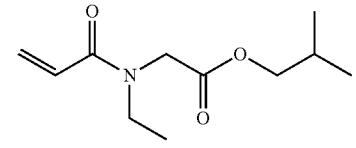
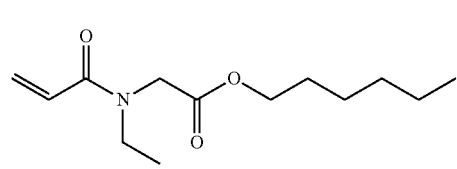

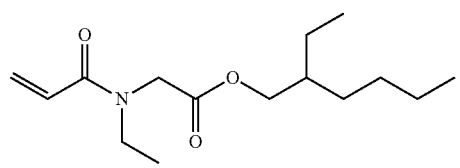
d2-8
Illustrated Compound of Group d3
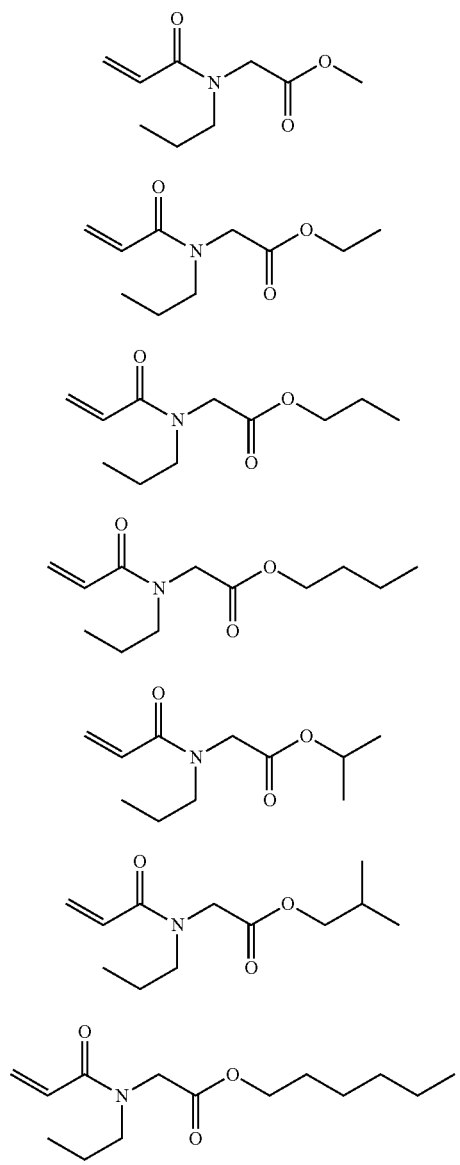
d3-1
d3-2
d3-3
d3-4
d3-5
d3-6
d3-7
d3-8
Illustrated Compound of Group d4
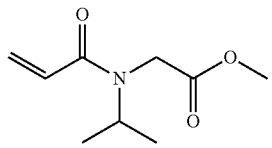
d4-1
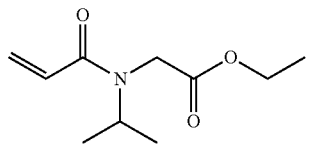
d4-2
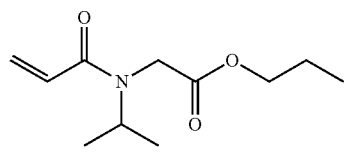
d4-3
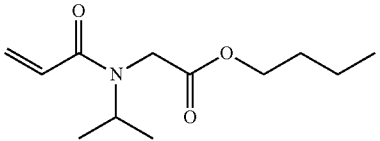
d4-4
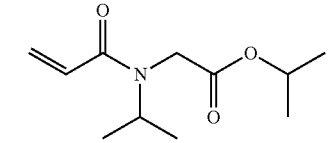
d4-5
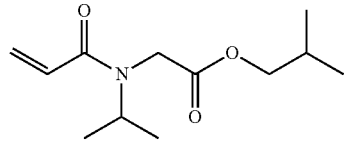
d4-6
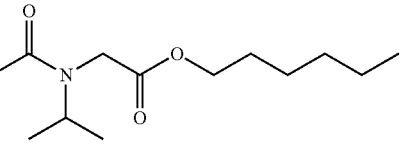
d4-7
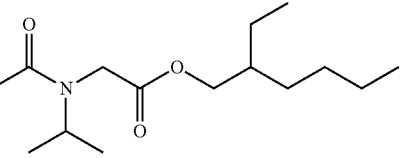
d4-8
Illustrated Compound of Group d5
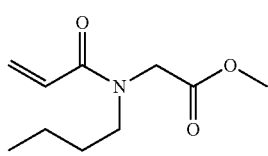
d5-1

-continued
d5-2
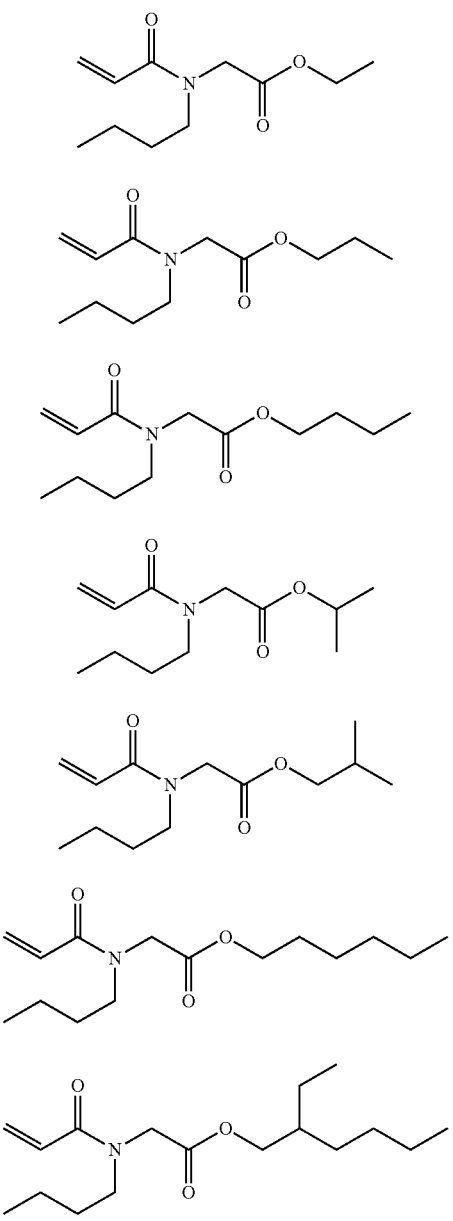
d5-3
d5-4
d5-5
d5-6
d5-7
d5-8
Illustrated Compound of Group d6
d6-1
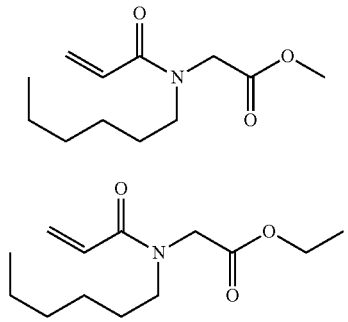
d6-2
d6-3
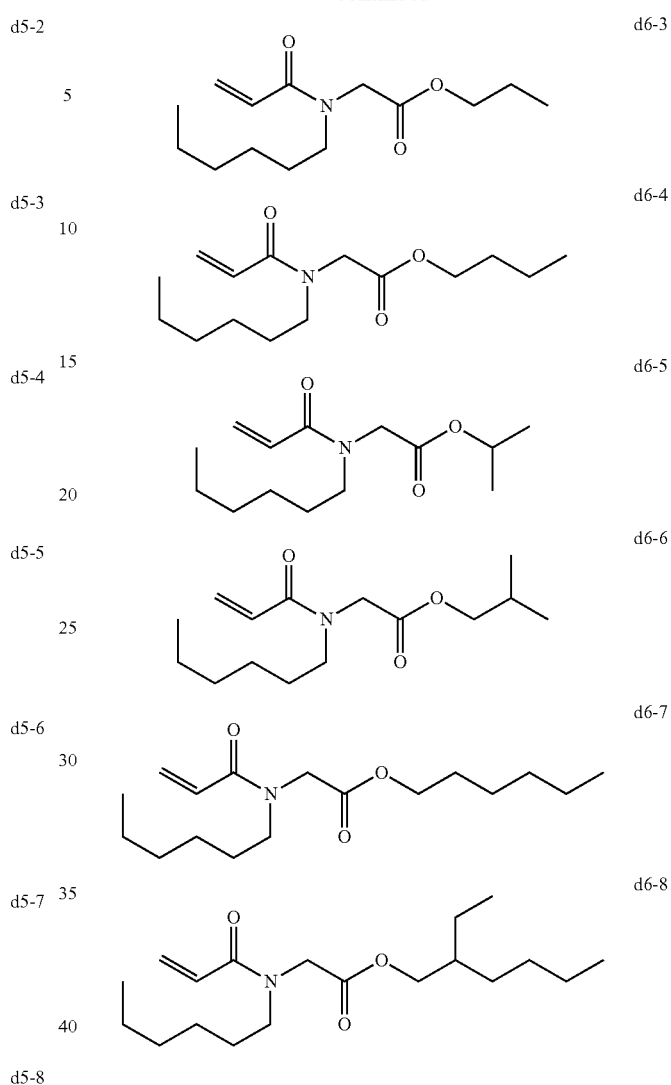
d6-4
d6-5
d6-6
d6-7
d6-8
Specific examples of the illustrated compound of group e include, but are not limited to, the compounds of group e1 to group e6 below. These can be used alone or in combination.
Illustrated Compound of Group e1
e1-1
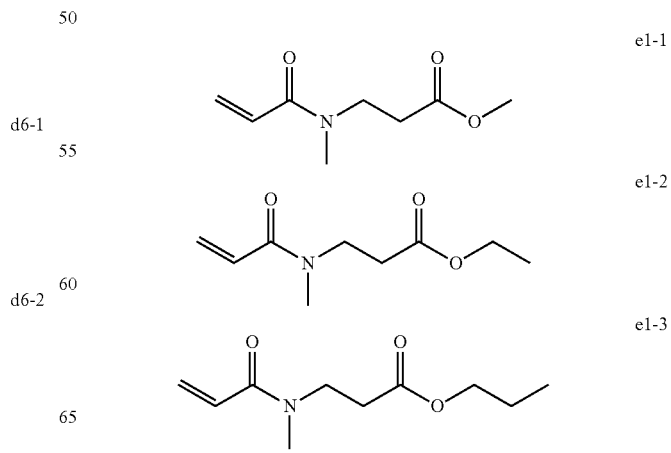
e1-2
e1-3

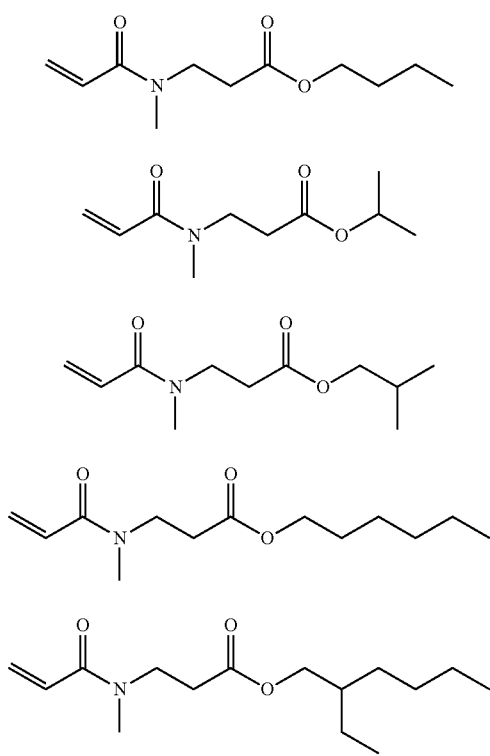
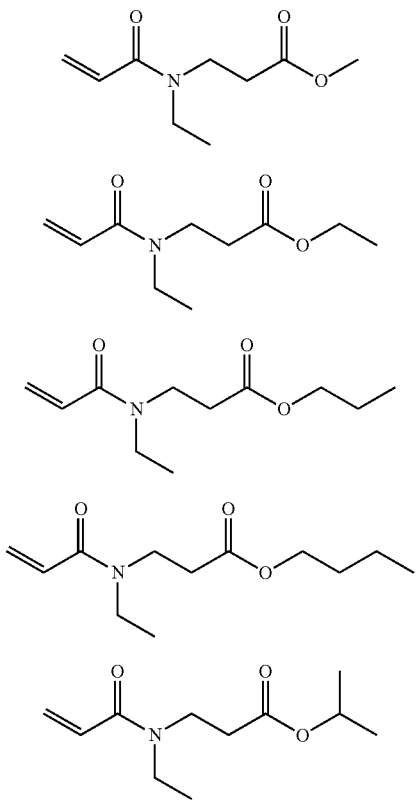
Illustrated Compound of group e2
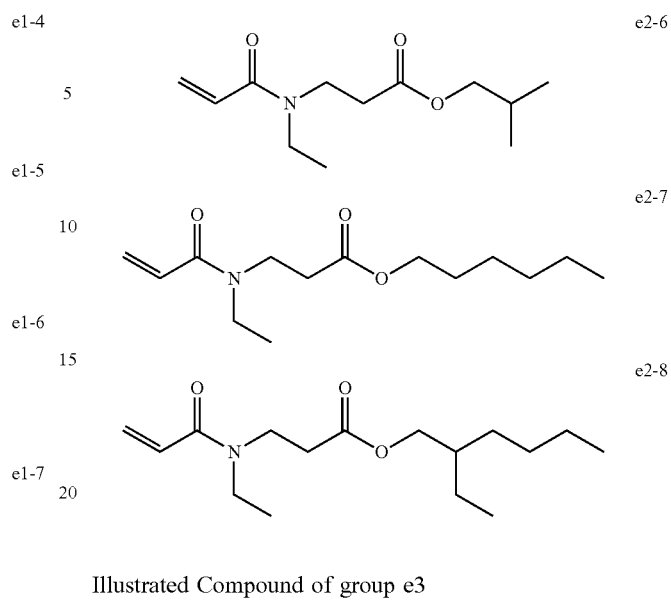
Illustrated Compound of group e3
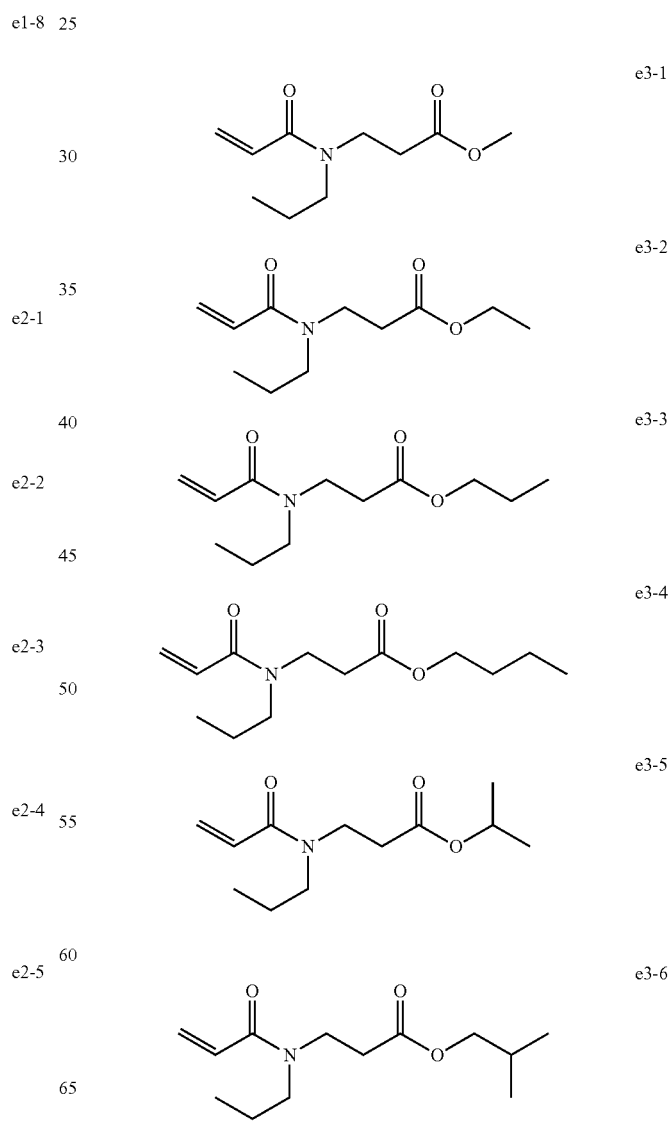

-continued
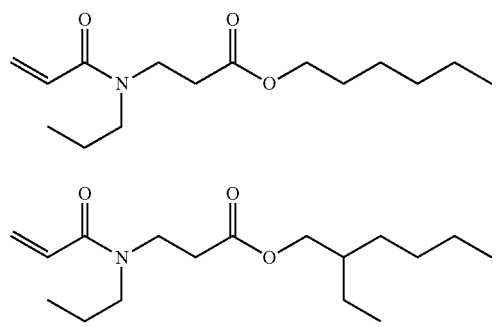
e3-7
e3-8
Illustrated Compound of Group e4
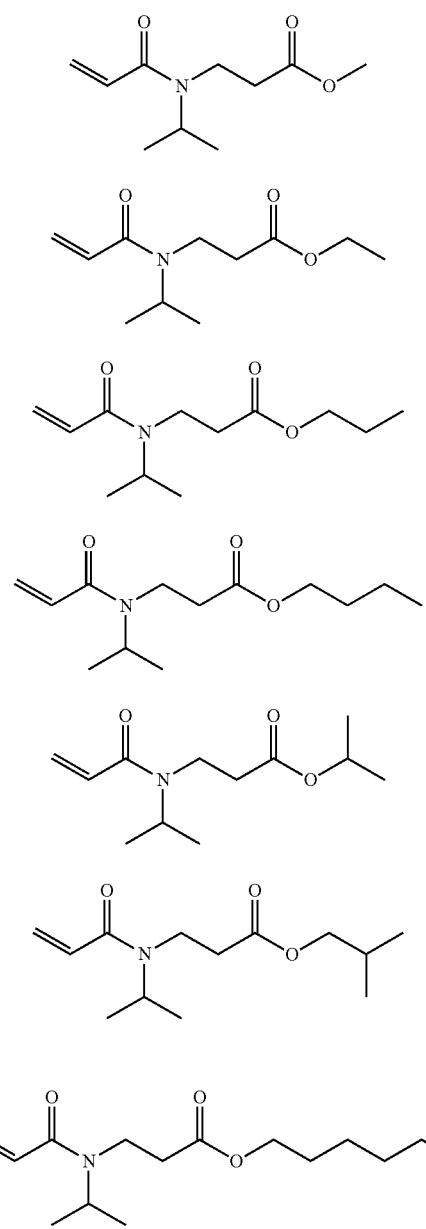
e4-1
e4-2
e4-3
e4-4
e4-5
e4-6
e4-7
-continued
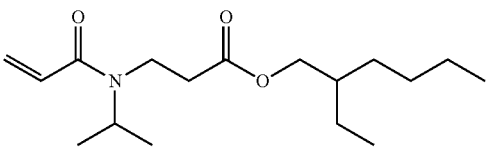
e4-8
Illustrated Compound of Group e5
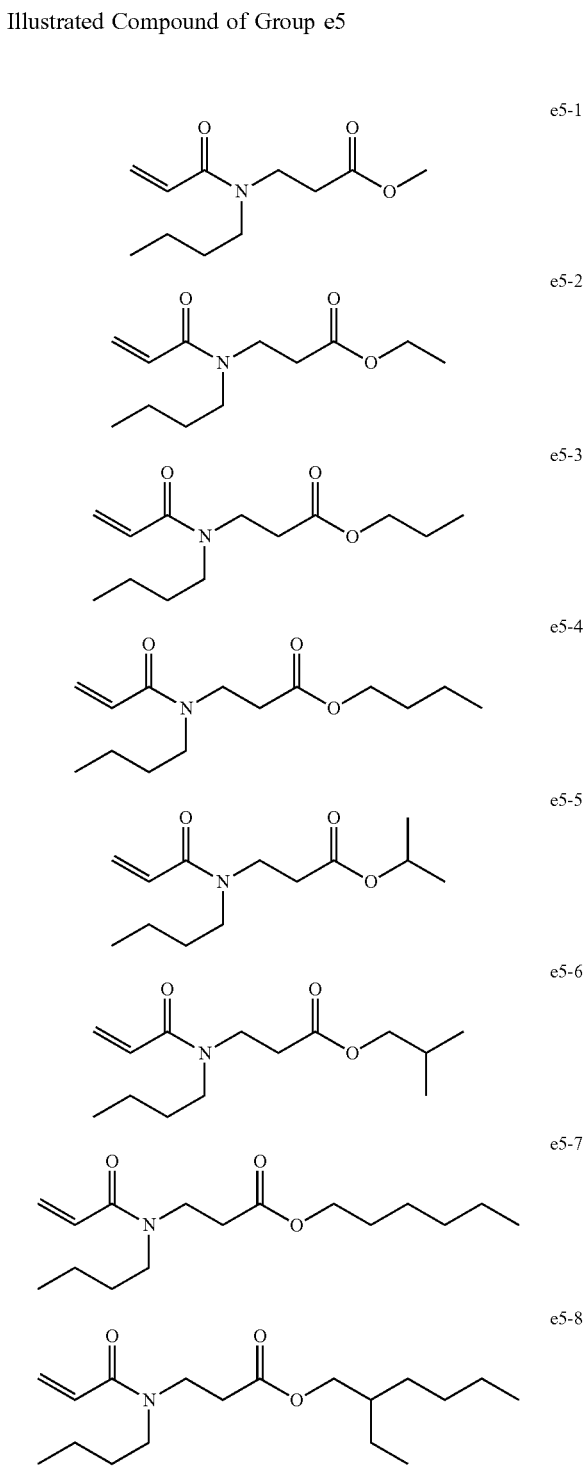
e5-1
e5-2
e5-3
e5-4
e5-5
e5-6
e5-7
e5-8

Illustrated Compound of Group e6

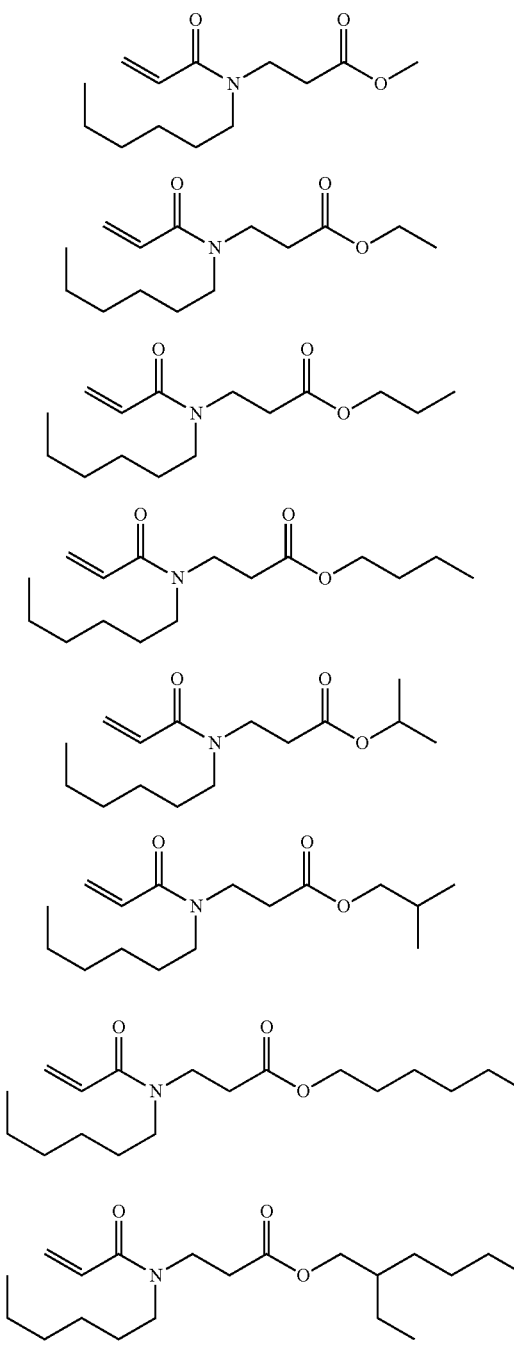

Specific examples of the illustrated compound of group f include, but are not limited to, the compounds of group f1. These can be used alone or in combination.
Illustrated Compound of Group f1

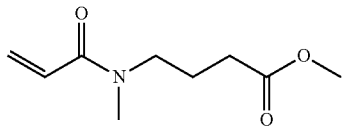

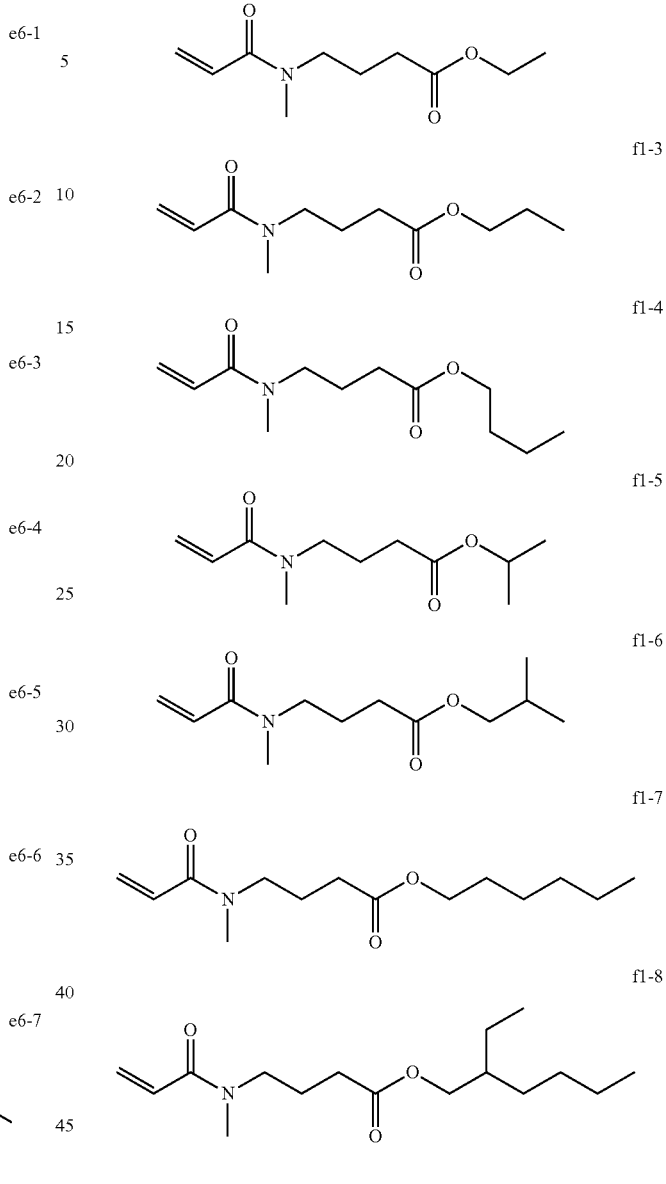

Specific examples of the illustrated compound of group g compound include, but re not limited to, the compounds of group g1 to group g6 below. These can be used alone or in combination.
Illustrated Compound of Group g1

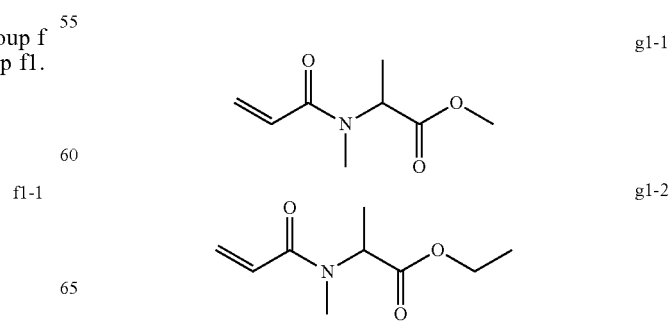

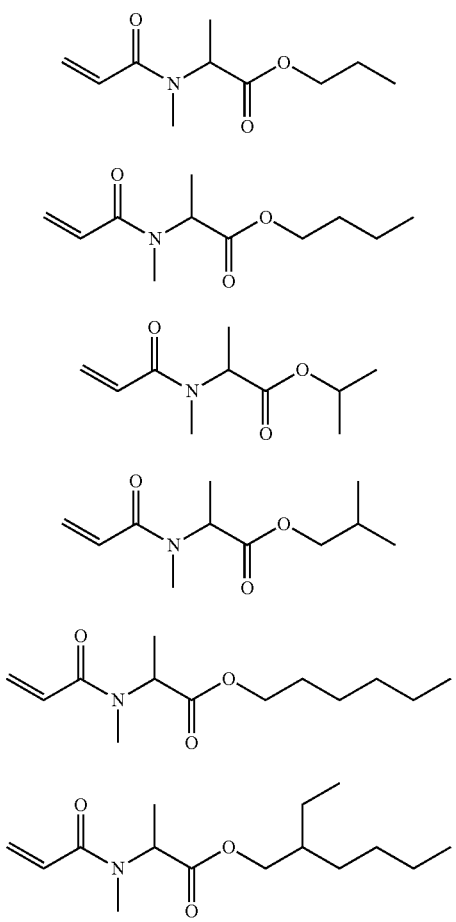
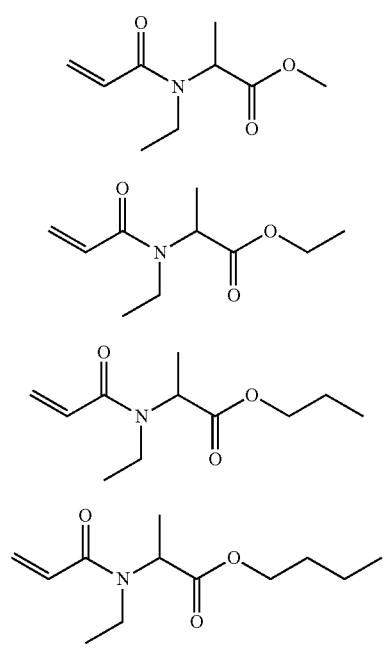
Illustrated Compound of Group g2
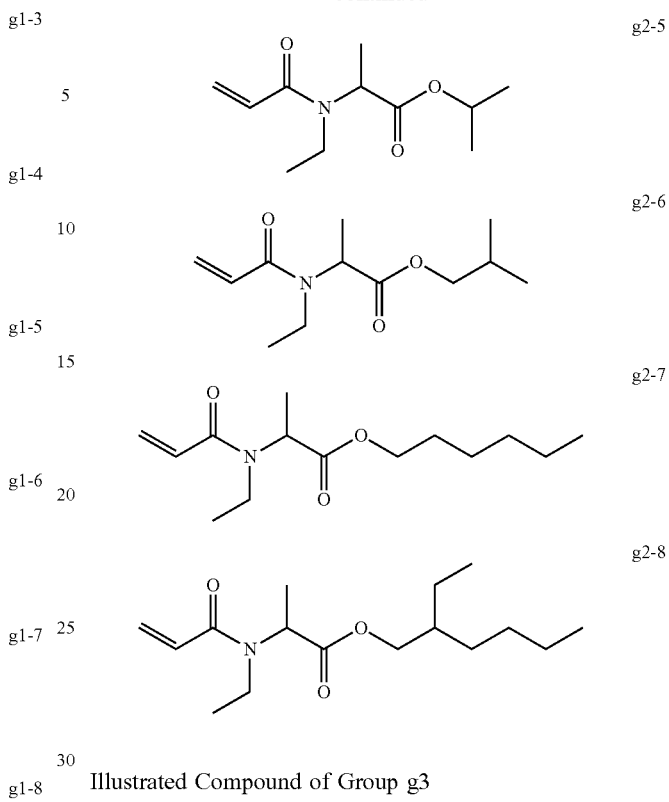
Illustrated Compound of Group g3

-continued
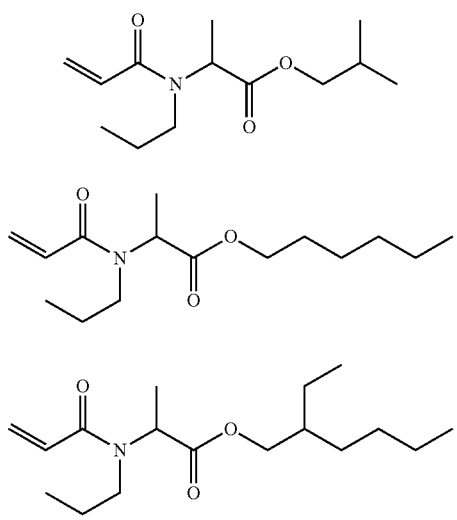
g3-6
g3-7
g3-8
Illustrated Compound of Group g4
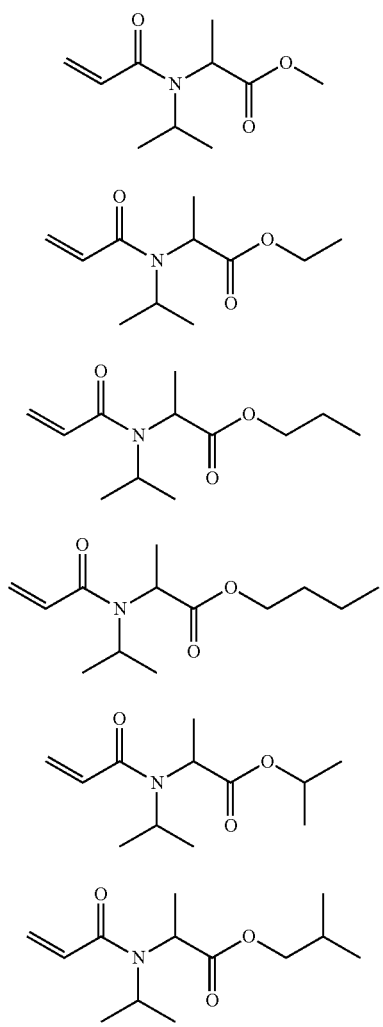
g4-1
g4-2
g4-3
g4-4
g4-5
g4-6
-continued
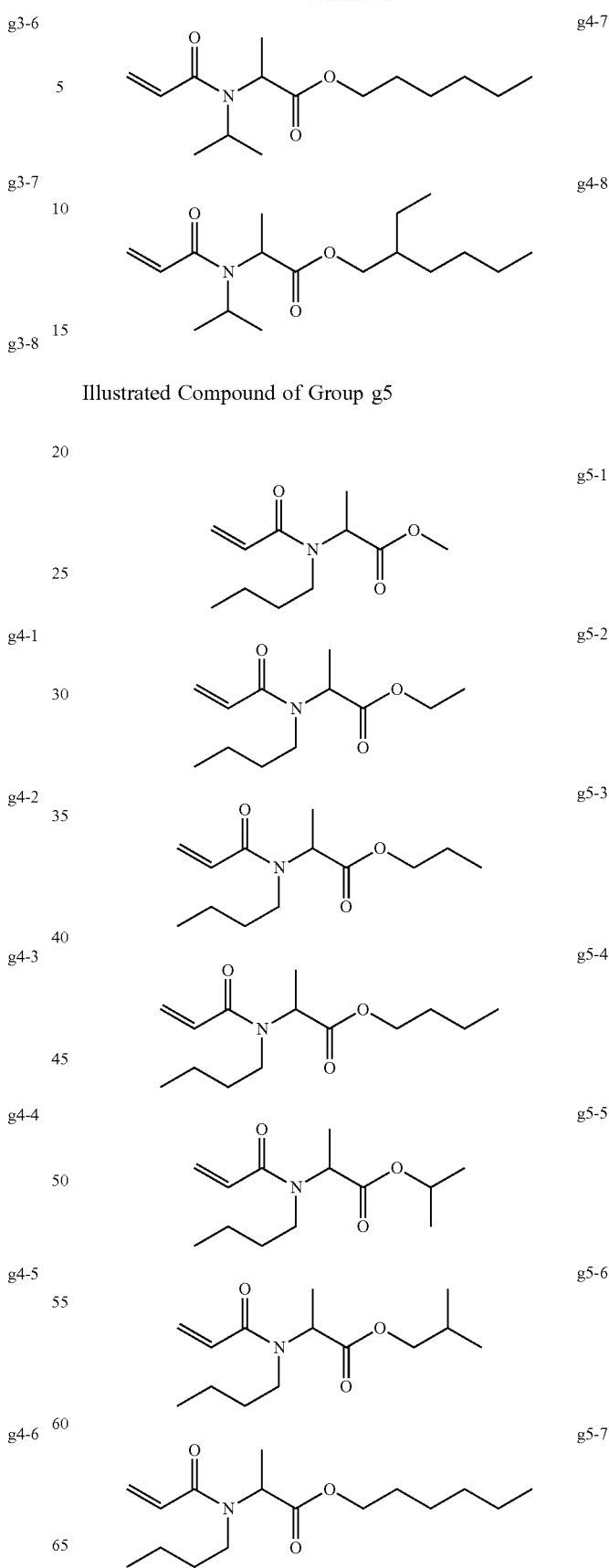
g4-7
g4-8
Illustrated Compound of Group g5
g5-1
g5-2
g5-3
g5-4
g5-5
g5-6
g5-7

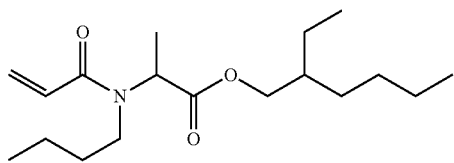

Illustrated Compound of group g6

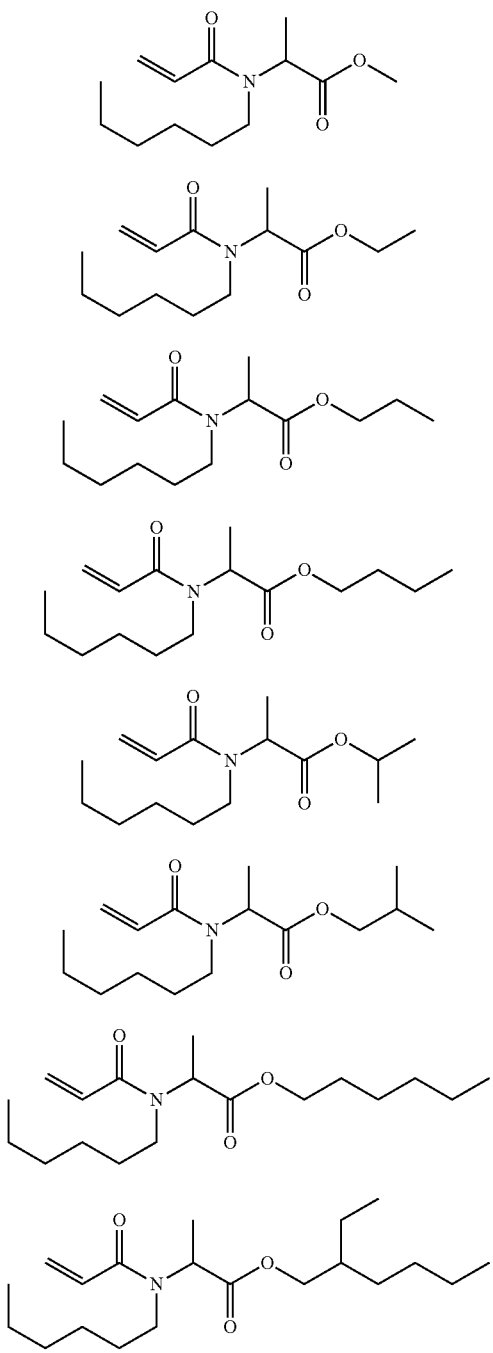

Specific examples of the illustrated compound of group h include, but are not limited to, the compounds of group h1 below.

These can be used alone or in combination.

Illustrated Compound of Group h1

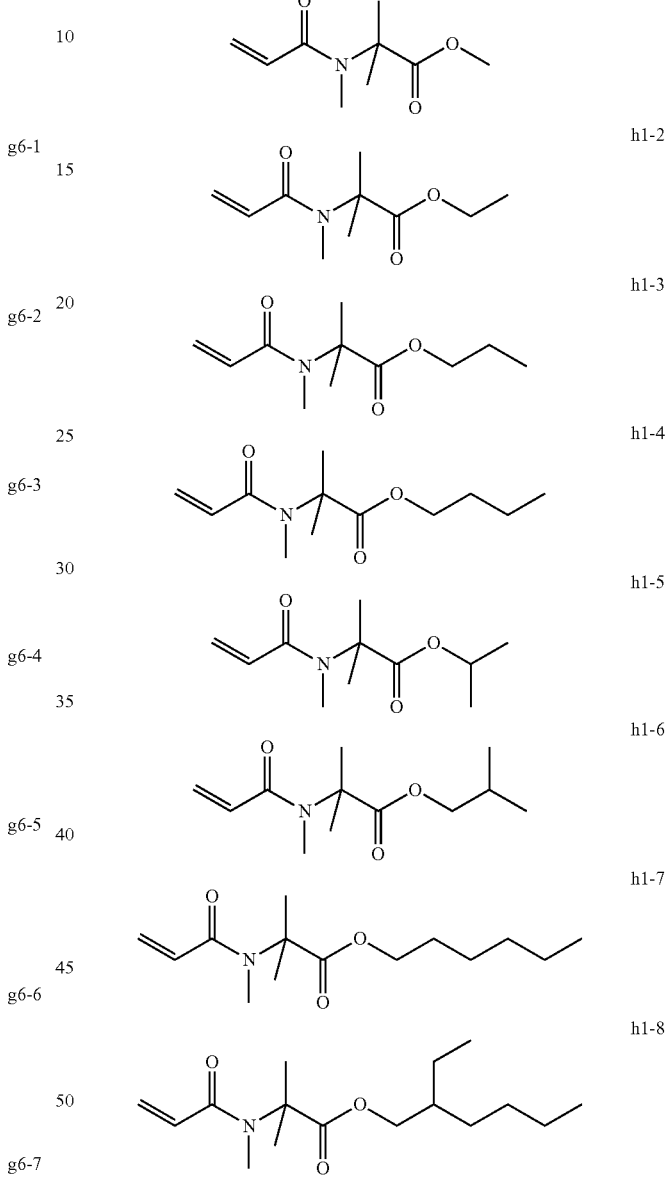

Of the illustrated compounds from group a to group h, the illustrated compounds a1-1, the illustrated compounds a1-4, the illustrated compounds a6-1, the illustrated compounds d1-1, the illustrated compounds d1-2, the illustrated compounds d1-4, the illustrated compounds d1-5, the illustrated compounds d3-2, the illustrated compounds d4-1, the illustrated compounds d4-5, the illustrated compounds d6-1, the illustrated compounds d6-4, the illustrated compounds g1-1, the illustrated compounds g1-2, and the illustrated compounds g1-5 are preferable and the illustrated compounds d1-1, the illustrated compounds d1-2, the illustrated compounds g1-1, the illustrated compounds g1-2, and the illustrated compounds g1-5 are more preferable.

The acrylamide compound represented by the Chemical formula 1 includes a mixture of two or more kinds of different compounds. The different compounds include structural isomers. The mixing ratio is not particularly limited.

The proportion of the acrylamide compound represented by the Chemical formula 1 is preferably from 20 to 98 percent by mass, more preferably from 30 to 90 percent by mass, and furthermore preferably from 30 to 80 percent by mass to the total content of a curable composition.

The structure of the acrylamide compound represented by the Chemical formula 1 can be analyzed using $^1$H-NMR spectrum and IR spectrum.

Other Curable Compound

As the other curable compound, curable compounds other than the acrylamide compound represented by the Chemical formula 1 can be used.

The other curable compounds other than the acrylamide compound represented by the Chemical formula 1 has no specific limit and can be suitably selected to suit to a particular application. Examples are radical polymerizable compounds, cationic polymerizable compounds, and anionic polymerizable compounds. These can be used alone or in combination.

The radical polymerizable compound has no particular limit and can be suitably selected to suit to a particular application as long as it contains at least one radically-polymerizable ethylenic unsaturated group. Examples are compounds containing monomers, oligomers, and polymers. Of these, unsaturated carboxylic acids such as acrylic acid, methacrylic acid, itaconic acid, crotonic acid, isocrotonic acid, and maleic acid, salts thereof, compounds derived therefrom, anhydrides having ethylenic unsaturated group, acrylonitrile, styrene, unsaturated polyester, unsaturated polyether, unsaturated polyamide, and unsaturated urethane.

Specific examples of the radical polymerizable compound include, but are not limited to, acrylic acid derivatives such as 2-hydroxyethylacrylate, buthoxyethylacrylate, carbitol acrylate, cyclobhexylacrylate, tetrahydroiurfurylacrylate, benzylacrylate, bis(4-acryloxy polyethoxyphenyl)propane, neopentyl glycoldiacrylate, ethoxylated neopentylglycol diacrylate, propoxylated neopentylglycol diacrylate, 1,6-hexanediolacrylate, ethyleneglycol diacrylate, diethylene glycoldiacrylate, triethylene glycoldiacrylate, tetraethylene glycoldiacrylate, polyethyleneglycol diacrylate, propyleneglycol diacrylate, dipropylene glycoldiacrylate, tripropylene glycol diacrylate, tetrapropylene glycoldiacrylate, polypropylene glycoldiacrylate, pentaerythritol triacrylate, pentaerythritol tetraacrylate, dipentaerythritol triacrylate, dipentaeythritol tetraacrylate, triimethylol propane triacrylate, tetramethylol methane traacrylate, oligoesteracrylate, and epoxyacrylate, methacrylic acid derivatives such as methylmethacrylate, n-butylmethacrylate, allylmethacrylate, glycidylmethacrylate, benzylmethacrylate, dimethylaminomethylmethacrylate, 1,6-hexythanediol dimethacrylate, ethyleneglycol dimethacrylate, triethyleneglycol dimethacrylate, polyethyleneglycol dimethacrylate, trimethylolethane trimethacrylate, trimethylol propane trimethacrylate, and 2,2-bis(4-methacryloyloxy polyethoxyphenyl)propane, acrylamide derivatives such as N-methylholacrylamide, diacetone acrylamide, 2-hydroxyethyl acrylamide, and acryloyl morphorine, derivatives of ally compounds such as allyl glycidyl ether, diallylphthalate, and triallyltrimellitate, monovinylether compounds, divinylether compounds, and trivinylether such as ethylene glycol divinylether, ethylene glycol mnovinylether, diethylene glycol divinylether, triethylene glycol monovinylether, triethyleneglycol divinylether, propylene glycol divinylether, diproppylene glycol divinylether, butanediol divinylether, hexane dioldivinylether, cyclohexane dimethanol divinylether, hydroxyethylmonovinylether, hydroxynonylmonovinylether, and trimethylolpropane trivinylether, monovinylether compounds such as ethylvinylether, n-butylvinylether, isobutylvinylether, octadecylvinylether, cyclohexylvinylether, hydroxydibutylvinylether, 2-ethylhexylvinylether, cyclohexane dimethanol monovinylether, n-propylvinylether, isopropyle vinylether, isopropenylether-o-propylene carbonate, dodecylvinylether, diethyleneglycol monovinylether, and octadecylvinylether, 2-ethylhexyldiglycolacrylate, 2-hydroxy-3-phenoxypropylacrylate, 2-hydroxybutylacrylate, hydroxy pivalic acid neopentyl glycoldiacrylate, 2-acryloyloxyethyl phthalate, methoxypolyethylene glycol acrylate, tetrramethylol methane triacrylate, 2-acryloyloxyethyl-2-hydroxyethyl phthalate, dimethylotricyclodecane diacrylate, ethoxylated phenyl acrylate, 2-acryloyloxy ethylsuccinate, an acrylate of adduct of nonylphenol with ethylne oxide, modified glycerin triacrylate, an adduct of bisphenol A with diglycidyl ether acryate, modified bispheno A diacrylate, phenoxypolyethylene glycol acaylate, 2-acryloyloxyethyl hexahydrophthalic acid, diacrylate of an adduct of bisphenol A with propylene oxide, diacrylate of an adduct of bisphenol A with ethylene oxide, dipentaerythritol hexaucrylate, trylenediisocyanate urethane prepolymer, lactone modified flexible acrylate, buthoxyethylacrylate, an adduct of propylene glycol with diglycidyl ether acrylate, hexamethylene diisocyanate urethane prepolymer, methoxydipropylene glycol acrylate, ditrimethylol propanetetraacrylate, stearylacrylate, isoamilacrylate, isomyristyl acrylate, isostearyl acrylate, and lactone-modified acrylate. These can be used alone or in combination.

Specific examples of the cationic polymerizable compound include, but are not limited to, epoxy compounds, vinylether compounds, and oxetane compounds. These can be used alone or in combination.

Specific examples of the anionic polymerizable compound include, but are not limited to, epoxy compounds, lactone compounds, acrylic compounds, and methacryl compounds. These can be used alone or in combination. Of these, acrylic acid derivatives and methacrylic acid derivatives illustrated as the radical polymerizable compound are preferable.

The proportion of the curable compounds is preferably from 0.01 to 100 parts by mass and more preferably from 0.1 to 50 parts by mass to 100 parts by mass of the acrylamide compounds represented by the Chemical formula 1.

Polymerization Initiator

The curable composition of the present disclosure may contain a polymerization initiator. The polymerization initiator produces active species such as a radical or a cation upon application of energy and initiates polymerization of a polymerizable compound (monomer or oligomer). As the polymerization initiator, it is suitable to use a known radical polymerization initiator, cation polymerization initiator, base producing agent, or a combination thereof. Of these, radical polymerization initiators are preferable. Moreover, the polymerization initiator preferably accounts for 5 to 20 percent by mass of the total content (100 percent by mass) of the composition to obtain sufficient curing speed.

Specific examples of the radical polymerization initiators include, but are not limited to, aromatic ketones, acylphosphineoxide compounds, aromatic oniumchlorides, organic peroxides, thio compounds (thioxanthone compounds, compounds including thiophenyl groups, etc.), hexaarylbiimidazole compounds, ketoxime-esterified compounds, borate compounds, azinium compounds, metallocene compounds, active ester compounds, compounds having a carbon halogen bond, and alkylamine compounds.

In addition, a polymerization accelerator (sensitizer) can be optionally used together with the polymerization initiator. The polymerization accelerator is not particularly limited. Preferred examples thereof include, but are not limited to, amine compounds such as trimethylamine, methyldimethanolamine, triethanolamine, p-diethylaminoacetophenone, p-dimethylaminoethylbenzoate, p-dimethyl aminobenzoate-2-ethylhexyl, N,N-dimthylbenzylamine, and 4,4'-bis(diethylamino)benzophenone. The content can be suitably determined to suit to the identification and the content of the polymerization initiator used in combination with the polymerization accelerator.

Specific examples of the cationic polymerization initiator include, but are not limited to, salts of $B(C_6F_5)_4^-$; $PF_6^-$; $AsF_6^-$, $SbF_6^-$, $CF_3SO_3^-$ of aromatic onium compounds such as diazonium, ammonium, iodonium, sulfonium, and phosphonium, sulfonated compounds capable of producing sulfonic acid, halogenated compounds producing halogenated hydrogen, and iron arene complex.

Specific examples of the anionic polymerization initiator include, but are not limited to, o-nitrobenzylcarbamate derivatives, o-acyloxyl derivatives, and o-carbamoyl oxime-amidine derivatives.

Examples of the combination of the curable compounds and the polymerization initiator are a combination of the radical polymerization compound and the radical polymerization initiator, a combination of the cationic polymerizable compound and the cationic polymerization initiator, and a combination of the anionic polymerizable compound and the anionic polymerization initiator.

Organic Solvent

The curable composition may include an organic solvent, but if possible, it is preferred that the composition be free of an organic solvent. The curable composition free of an organic solvent, in particular volatile organic compound (VOC), is preferable because it enhances safeness at where the composition is handled so that pollution of the environment can be prevented. The organic solvent represents a conventional non-reactive organic solvent, for example, ether, ketone, xylene, ethylacetate, cyclohexanone, and toluene, which is clearly distinguished from reactive monomers. Furthermore, "free of" an organic solvent means that no organic solvent is substantially included. The proportion is preferably less than 0.1 percent by mass.

Coloring Material

The curable composition of the present disclosure may contain a coloring agent. As the coloring agent, although depending on the objectives and requisites of the composition in the present disclosure, various pigments and dyes can be used, which impart black, white, magenta, cyan, yellow, green, orange, and gloss color such as gold and silver. The proportion of the coloring agent is not particularly limited. It can be determined considering the desired color density and dispersibility of the coloring agent in the curable composition, etc. It is preferred that the proportion of the coloring agent account for 0.1 to 20 percent by mass of the total content (100 percent by weight) of the composition. The curable composition of the present disclosure does not necessarily include a coloring material but can be clear and colorless.

If the curable composition contains no coloring material, the composition is suitable as an overcoat layer to protect images.

As the pigment, an inorganic or organic pigment can be used alone or in combination.

Specific examples of the inorganic pigment include, but are not limited to, carbon blacks (C.I. Pigment Black 7) such as furnace black, lamp black, acetylene black, and channel black, iron oxides, and titanium oxides.

Specific examples of the organic pigment include, but are not limited to, azo pigments such as insoluble azo pigments, condensed azo pigments, azo lakes, and chelate azo pigments, polycyclic pigments such as phthalocyanine pigments, perylene pigments, perinone pigments, anthraquinone pigments, quinacridone pigments, dioxane pigments, thioindigo pigments, isoindolinone pigments, and quinofuranone pigments, dye chelates such as basic dye type chelates, acid dye type chelates, dye lakes such as basic dye type lake and acid dye type lake, nitro pigments, nitroso pigments, aniline black, and daylight fluorescent pigments.

In addition, a dispersant is optionally added to enhance dispersibility of a pigment. The dispersant has no particular limit. For example, it is suitable to use polymer dispersants conventionally used to prepare a pigment dispersion.

The dye includes, for example, an acidic dye, a direct dye, a reactive dye, a basic dye, and a combination thereof.

Other Components

The curable composition of the present disclosure may furthermore optionally include other known components. The other known components are not particularly limited. Examples are known articles such as surfactants, polymerization inhibitors, leveling agents, defoaming agents, fluorescent brighteners, penetration-enhancing agents, wetting agents (humectants), fixing agents, viscosity stabilizers, fungicide, preservatives, antioxidants, ultraviolet absorbents, chelate agents, pH regulator, and thickeners.

Polymerization Inhibitor

The polymerization inhibitor improves storage property (storage stability) of the curable composition and can prevent head clogging ascribable to thermal polymerization when discharging the curable composition while the curable compound is heated and viscosity thereof is reduced.

The polymerization inhibitor has no particular limit. Specific examples include, but are not limited to, hydroquinone, benzoquinone, p-methoxyphenol, TEMPO, TEMPOL, and cupferron complex of aluminum. These can be used alone or in combination.

The proportion of the polymerization inhibitor is preferably from 200 to 20,000 ppm.

Sensitizer

The curable composition of the present disclosure may furthermore optionally include, a sensitizer to accelerate decomposition of a polymerization initiator upon application of energy.

When the sensitizer absorbs active energy rays and heat, it is excited. Thereafter, the sensitizer in the excited state is brought into contact with a polymerization initiator so that chemical change (decomposition or production of radicals, acids, or bases) of the polymerization initiator is accelerated due to the action of electron moving, energy transfer, generation of heat, etc.

The mass ratio (A/B) of the content A (percent by mass) of the sensitizer to the content B (percent by mass) of the polymerization initiator is preferably from $5 \times 10^{-3}$ to 200 and more preferably from 0.02 to 50.

The sensitizer has no particular limit and can be suitably selected to suit to a particular application. For example, a sensitizing dye absorbing wavelengths in the wavelength area of from 350 to 450 nm is suitable.

Specific examples of the sensitizing dye include, but are not limited to, polynuclear aromatic series (for example, pyrene, perylene, and triphenylene), xanthenes (for example, flourescein, eosin, erythrosine, Rhodamine B, and rose bengal), cyanines (for example, thiacarbocyanine, and oxacarbocyanine, merocyanines (for example, merocyaninem and carbomerocyanine), thiadines (for example, thionine, methylene blue, and toluidine blue), acrydines (for example, acaydine oange, chloroflavin, and acriflavine), anthraquinones (for example, anthraquinone), squaryliums (for example, squarylium), and coumarins (for example, 7-diethylamino-4-methyl coumarin). These can be used alone or in combination.

Sensitizer

The curable composition of the present disclosure may furthermore optionally contain a co-sensitizer.

For example, co-sensitizers can furthermore improve sensitivity to active energy rays of the sensitizing dye or heat and reduce polymerization inhibition of the curable compound by oxygen.

The co-sensitizer has no particular limit and can be suitably selected to suit to a particular application.

Specific examples include, but are not limited to, amine-based compounds such as triethanol amine, p-dimethylamino benzoic acid ethylester, p-formyl dimethylaniline, and p-methylthiodimethylaniline, thiol such as 2-mercapto benzothiazol, 2-mercaptobenzooxazol, 2-mercaptobenzoimidazol, 2-mercapto-4(3H)-quinazoline, and P-mercaptonaphthalene, and sulfides. These can be used alone or in combination.

Solvent

It is preferable that the curable composition be free of a solvent. However, for example, to increase attachability between a recording medium and ink after being cured, it is possible to contain a solvent only when the solvent does not slow down the curing speed of ink, etc.

The solvent has no specific limit. Examples are organic solvents and water. These can be used alone or in combination.

The proportion of the solvent to the total mass of the curable composition is preferably from 0.1 to 5 percent by mass and more preferably 0.1 to 3 percent by mass.

The curable composition of the present disclosure may furthermore optionally contain a surfactant, a leveling additive, a matte agent, and polyester resins, polyurethane resins, vinyl resins, acrylic resins, rubber resins, and wax to adjust properties of film.

In addition, the curable composition of the present disclosure may furthermore optionally contain a viscosity imparting agent (tackifier) to improve attachability to polyolefin film, PET film, etc.

The surfactant has no specific limit and can be suitably selected to suit to a particular application. Examples are higher aliphatic acid surfactants, silicone surfactants, and fluorochemical surfactants.

Curing Method

An example of the method of curing the curable composition of the present disclosure is curing upon application of energy.

Specific example of the energy include, but are not limited to, heat and active energy rays. These can be used alone or in combination. Of these, active energy rays are preferable.

Curing Device

The device to cure the curable composition of the present disclosure utilizes curing upon application of heat or active energy rays. Curing upon application of active energy rays is preferable.

The active energy rays for use in curing the curable composition of the present disclosure are not particularly limited as long as they can apply energy to conduct polymerization reaction of the polymerizable components in the curable composition.

Specific examples include, but are not limited to, electron beams, α rays, ß rays, γ rays, and X rays, in addition to ultraviolet rays. A particularly high energy light source obviates the need for a polymerization initiator to proceed polymerization reaction. In addition, in the case of irradiation of ultraviolet rays, mercury-free is strongly demanded in terms of protection of environment. Therefore, replacement with GaN-based ultraviolet light-emitting devices is greatly preferred from industrial and environmental point of view. Furthermore, ultraviolet ray light-emitting diode (UV-LED) and ultraviolet ray laser diode (UV-LD) are preferable.

Small size, long working life, high efficiency, and high cost performance thereof make such irradiation sources desirable as an ultraviolet light source.

Preparation of Curable Composition

The curable composition of the present disclosure can be prepared by using the components mentioned above. The preparation devices and conditions are not particularly limited.

For example, the curable composition can be prepared by loading a polymerizable monomer, a pigment, a dispersant, etc., into a dispersing machine such as a ball mill, a kitty mill, a disk mill, a pin mill, and a DYNO-MILL to prepare a pigment liquid dispersion followed by mixing with a polymerizable monomer, an initiator, a polymerization inhibitor, and a surfactant.

Viscosity

Viscosity of the curable composition of the present disclosure has no particular limit and can be suitably adjusted to suit to a particular application and a particular device. For example, if discharging device that discharges the composition from nozzles is used, viscosity thereof is preferably in a range of from 3 to 40 mPa·s, more preferably from 5 to 15 mPa·s, and particularly preferably from 6 to 12 mPa·s in a temperature range of from 20 to 65 degrees C., preferably at 25 degrees C. In addition, it is particularly preferable to satisfy this viscosity range without including the organic solvent mentioned above. Viscosity can be measured by a cone-and-plate type rotary viscometer (VISCOMETER TVE-22L, manufactured by TOKI SANGYO CO., LTD.) using a cone rotor (1°34'×R24) at a number of rotation of 50 rpm with a setting of the temperature of hemathermal circulating water in a range of from 20 to 65 degrees C. VISCOMATE VM-150III can be used for the temperature control of the circulating water.

Application Field

The application field of the curable composition of the present disclosure is not particularly limited. It can be applied to any field where the active energy ray curable composition is used. For example, the curable composition is selected to a particular application and used for a resin for molding, a paint, an adhesive, an insulant, a release agent, a coating material, a sealing material, various resists, and various optical materials.

Figure 2:
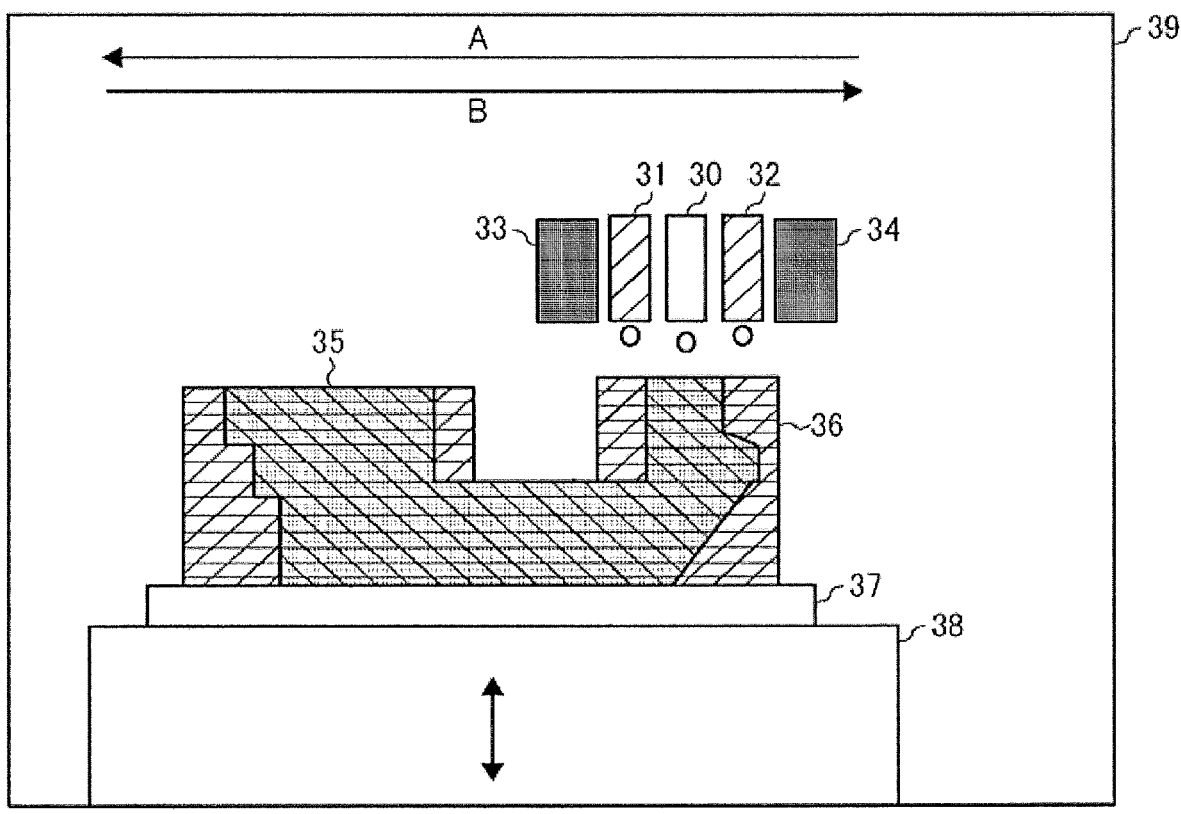
FIG. 2 is a schematic diagram illustrating another example of the image forming device according to an embodiment of the present disclosure.
Figure 3A:
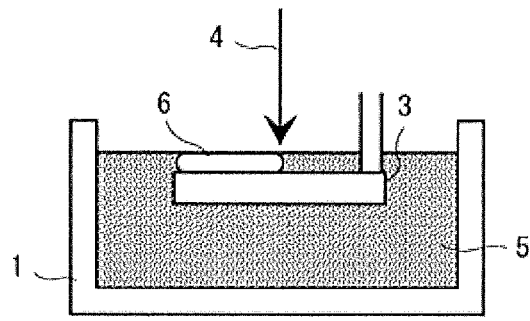
FIGS. 3A, 3B, 3C, and 3D are schematic diagrams illustrating yet another example of the image forming device according to an embodiment of the present disclosure.
Figure 3B:
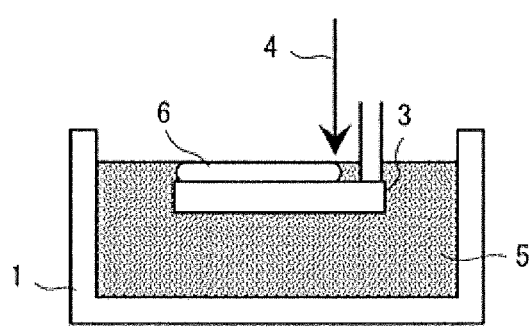
Figure 3C:
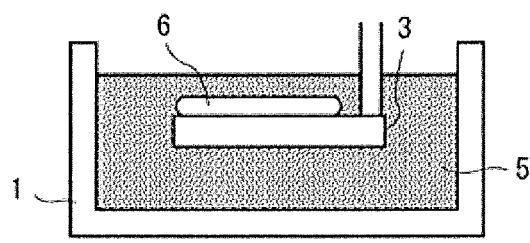
Figure 3D:
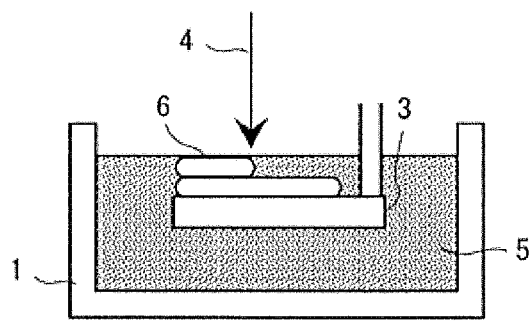

Furthermore, the curable composition of the present disclosure can be used as an ink to form two-dimensional texts, images, and designed coating film on various substrates and in addition a solid object forming material to form a three-dimensional image (solid freeform fabrication object). This material for a solid freeform fabrication can be used as a binder for powder particles for use in powder additive manufacturing to conduct solid freeform fabrication by repeating curing and laminating powder layers. Also, it can be used as a solid constituting material (modeling material) or supporting member (supporting material) for use in additive manufacturing (stereolithography) method as illustrated in FIG. 2 and FIGS. 3A to 3D. FIG. 2 is a diagram illustrating a method of discharging the curable composition of the present disclosure to a particular area followed by curing upon irradiation of active energy rays to form a layer and laminating the layers (detail of which is described later).

FIGS. 3A to 3D are diagrams illustrating a method of irradiating a pool (accommodating unit) 1 of the curable composition of the present disclosure with active energy rays 4 to form a cured layer 6 having a particular form on a movable stage 3 and sequentially laminating the cured layer 6 so that a solid freeform fabrication object is obtained.

A device for fabricating a three-dimensional object using the curable composition of the present disclosure is not particularly limited. Known devices can be used.

For example, a device includes an accommodating device, a supplying device, and a discharging device, and an irradiator of the curable composition.

In addition, the present disclosure includes cured matter obtained by curing the curable composition and processed products obtained by processing structures having the cured matter formed on a substrate. The molded product is fabricated by, for example, heating drawing and punching cured matter or structures having a sheet-like form or film-like form. For example, the molded product is preferably used when surface-processing is required to be conducted after decorating the surface such as gauges or operation panels of vehicles, office machines, electric and electronic machines, and cameras.

The substrate is not particularly limited. It can be suitably selected to suit to a particular application. Examples are fiber, threads, fabrics, leather, metal, plastic, glass, wood, ceramics, or composite materials thereof. Of these, plastic substrates are preferred in terms of processability.

Curable Ink

The curable ink of the present disclosure includes a curable composition of the present disclosure.

As the curable composition, the same curable composition of the present disclosure can be used.

For example, glossy resins, pigments, or dyes are added to the curable composition to obtain the curable ink.

The curable ink is preferably used for inkjet. Of the curable ink, those having low viscosity are suitably used as ink for inkjet printing.

Composition Accommodating Container

The composition accommodating container of the present disclosure means a container in which the curable composition is accommodated and is suitable for the applications as described above. For example, if the curable composition of the present disclosure is used for ink, a container that stores the ink can be used as an ink cartridge or an ink bottle. Therefore, users can avoid direct contact with the ink during operations such as transfer or replacement of the ink, so that fingers and clothes are prevented from being contaminated. Furthermore, inclusion of foreign matter such as dust in the ink can be prevented. In addition, the container can be of any size, any form, and any material. For example, the container can be designed to a particular application. It is preferable to use a light blocking material to block the light or cover a container with a light blocking sheet, etc.

The image forming device for two-dimensional images or three-dimensional images of the present disclosure includes an accommodating unit to accommodate at least one of the curable composition and the curable ink and energy applying device to apply energy.

The image forming method of two-dimensional images or three-dimensional images of the present disclosure includes applying energy to at least one of the curable composition and the curable ink to form two dimensional image or three dimensional images.

Image Forming Method and Image Forming Device

The image forming method of the present disclosure may utilize active energy rays, heating, etc. The image forming method of the present disclosure includes at least an irradiating step of irradiating the curable composition of the present disclosure with an active energy my to cure the curable composition. The image forming device of the present disclosure includes an irradiator to irradiate the curable composition of the present disclosure with an active energy ray and an accommodating unit to accommodate the curable composition of the present disclosure. The accommodating unit may include the container mentioned above. Furthermore, the method and the device may respectively include a discharging step and a discharging device to discharge the curable composition. The method of discharging the curable composition is not particularly limited. Examples are a continuous spraying method and an on-demand method. The on-demand method includes a piezo method, a thermal method, an electrostatic method, etc.

FIG. 1 is a diagram illustrating an image forming device including an inkjet discharging device. Printing units 23a, 23b, 23c, and 23d respectively having ink cartridges and discharging heads for yellow, magenta, cyan, and black curable inks discharge the inks onto a recording medium 22 supplied from a supplying roller 21. Thereafter, light sources 24a, 24b, 24c, and 24d to cure the inks emit active energy rays to the inks, thereby curing the inks to form a color image. Thereafter, the recording medium 22 is conveyed to a processing unit 25 and a printed matter reeling roll 26. Each of the printing unit 23a, 23b, 23c and 23d may include heating mechanism to liquidize the ink at the ink discharging portion. Moreover, a mechanism may be optionally disposed to cool down the recording medium to around room temperature in a contact or non-contact manner. In addition, the inkjet recording method may be either of serial methods of discharging an ink onto a recording medium by moving the head while the recording medium intermittently moves according to the width of a discharging head or line methods of discharging an ink onto a recording medium from a discharging head held at a fixed position while the recording medium continuously moves.

The recording medium 22 is not particularly limited.

Specific examples include, but are not limited to, paper, film, ceramics, glass, metal, or complex materials thereof. The recording medium 22 takes a sheet-like form but is not limited thereto. The image forming device may have a simplex printing configuration capable of printing on one side a recording medium or a duplex printing configuration capable of printing on both sides thereof. The recording medium is not limited to articles used as typical recording media. It is suitable to use building materials such as wall paper and floor material, cloth for apparel such as T-shirts, textile, and leather as the recording media.

Optionally, multiple colors can be printed with no or faint active energy rays from the light sources 24a, 24b, and 24c followed by irradiation of the active energy ray from the light source 24d. As a result, energy and cost can be saved.

The recorded matter having images printed with the ink of the present disclosure includes articles having printed images or texts on a plain surface of conventional paper, resin film, etc., articles having printed images or texts on a rough surface, or articles having printed image or texts on a surface made of various materials such as metal or ceramics. In addition, by laminating layers of two-dimensional images in part of a recording medium, a partially stereoscopic image (formed of two dimensional part and three-dimensional part) and a three dimensional objects can be fabricated.

FIG. 2 is a schematic diagram illustrating an example of the image forming device (device for fabricating a three-dimensional image) relating to the present disclosure. An image forming device 39 illustrated in FIG. 2 forms laminated layers while discharging a first curable composition from a discharging head unit 30 for fabrication object and a second curable composition composed of different ingredients from the first curable composition from discharging head units 31 and 32 for a support by using a head unit having inkjet heads arranged movable in the directions indicated by the arrows A and B and curing each composition by ultraviolet irradiators 33 and 34 placed adjacent to the discharging head units 31 and 32. More specifically, for example, the discharging head units 31 and 32 for a support discharge the second curable composition onto a substrate 37 for fabrication object and the second curable composition is solidified upon irradiation of active energy rays to form a first support layer having a pool. Thereafter, the discharging head unit 30 for fabrication object discharges the first curable composition onto the pool followed by irradiation of active energy rays for solidification, thereby forming a first fabrication object layer. This step is repeated multiple times while lowering a stage 38 movable in the vertical direction to laminate the support layer and the fabrication object layer to fabricate a solid freeform fabrication object 35. Thereafter, a laminated support 36 is removed, if desired. Although only a single discharging head unit 30 for fabrication object is provided in FIG. 2, the device may have two or more discharging head units 30.

Cured Matter

The cured matter is formed using at least one of the curable composition of the present disclosure and the curable ink of the present disclosure.

As the curable ink, the same curable ink can be used.

As the curable ink, the same curable ink can be used.

Decorated Object

A decorated object has a substrate on which a surface decoration made of cured matter is formed and the same curable matter can be used.

The substrate is not particularly limited. It can suitably be selected to suit to a particular application. Specific examples include, but are not limited to, paper, thread, fiber, fabrics, leather, metal, plastic, glass, wood, ceramics, or composite materials thereof. Of these, plastic substrates are preferred in terms of processability.

Having generally described preferred embodiments of this disclosure, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

Next, the present disclosure is described in detail with reference to Examples and Comparative Examples but not limited thereto.

In addition, $^1$H-NMR spectrum was measured using $^1$H-NMR (500 MHz, ECX500, manufactured by JEOL Ltd.). IR spectrum was measured using FT-IR (SpectrumGX, manufactured by PERKIN ELMER).

Having generally described preferred embodiments of this invention, further understanding can be obtained by reference to certain specific examples which are provided herein for the purpose of illustration only and are not intended to be limiting. In the descriptions in the following examples, the numbers represent weight ratios in parts, unless otherwise specified.

Example 1a 15.02 g (200 mmol) of 2-(methylamino)ethanol (manufactured by Tokyo Chemical Industry Co. Ltd.) was added to 200 mL of dehydrated dichloromethane and 46.8 g (462 mmol) of triethylamine was added thereto. Thereafter, the resultant was cooled in a mixture of dry ice and acetone to about −60 degrees C. Thereafter, 15.39 g (170 mmol) of acrylic acid chloride (manufactured by Wako Pure Chemical Industries, Ltd.) was diluted with 8 mL of dehydrated dichloromethane and slowly dripped to the resultant followed by stirring at room temperature for two hours. Again, the resultant was cooled in the mixture of dry ice and acetone to about −60 degrees C. Thereafter, 15.7 g (200 mmol) of acetylchloride was diluted with 8 mL of dehydrated dichloromethane and slowly dripped to the resultant followed by stirring at room temperature for about two hours. Moreover, after precipitates were removed by filtration, the filtrate was rinsed with water, an aqueous solution of saturated sodium hydrogen carbonate, and an aqueous solution of saturated sodium chloride. Thereafter, subsequent to drying with sodium sulfate, the resultant was condensed under a reduced pressure to obtain oily matter. Moreover, the oily matter was refined by column chromatography filled with 300 g of silicagel C-300 (manufactured by Wako Pure Chemical Industries, Ltd.) using hexane and ethyl acetate as eluate to obtain 6.1 g of light brown oily matter of the curable compound represented by the following Chemical structure a1-1 with a yield of about 21 percent.

Chemical structure a1-1

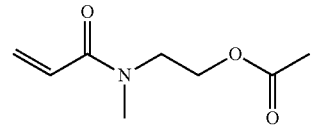

Identification data are as follows.

$^1$H-NMR (CDCl$_3$): δ2.04-2.08 (m, 3H), 3.04-3.15 (m, 3H), 3.63-3.71 (m, 2H), 4.20-4.27 (m, 2H), 5.69-5.72 (m, 1H), 6.32-6.37 (m, 1H), 6.56-6.63 (m, 1H)

IR(NaCl): 3474, 2957, 1740, 1649, 1612, 1450, 1418, 1407, 1378, 1235, 1137, 1047, 981, 795, 605 cm$^{-1}$

Example 2a 6.01 g (80 mmol) of 2-(methylamino)ethanol (manufactured by Tokyo Chemical Industry Co. Ltd.) was added to 120 mL of dehydrated dichloromethane and 18.7 g (185 mmol) of triethylamine was added thereto. Thereafter, the resultant was cooled in a mixture of dry ice and NaCl to about −15 degrees C. Thereafter, 6.15 g (68 mmol) of acrylic acid chloride (manufactured by Wako Pure Chemical Industries, Ltd.) was diluted with 4.5 mL of dehydrated dichloromethane and slowly dripped to the resultant followed by stirring at room temperature for two and a half hours. Again, the resultant was cooled in the mixture of dry ice and NaCl to about −15 degrees C. Thereafter, 8.52 g (80 mmol) of isobutylchloride was diluted with 4.5 mL of dehydrated dichloromethane and slowly dripped to the resultant followed by stirring at room temperature for about 3.5 hours. Moreover, after precipitates were removed by filtration, the filtrate was rinsed with water, an aqueous solution of saturated sodium hydrogen carbonate, and an aqueous solution of saturated sodium chloride. Thereafter, subsequent to drying with sodium sulfate, the resultant was condensed under a reduced pressure to obtain oily matter. Moreover, the oily matter was refined by column chromatography filled with 360 g of silicagel C-300 (manufactured by Wako Pure Chemical Industries, Ltd.) using hexane and ethyl acetate as eluate to obtain 2.2 g of pale yellow oily matter of the curable compound represented by the following Chemical structure a1-4 with a yield of about 16 percent.

Chemical structure a1-4

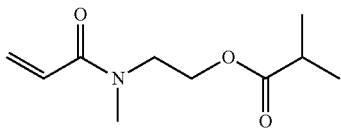

Identification data are as follows.

$^1$H-NMR (CDCl$_3$): δ 1.15-1.20 (m, 6H), 2.52-2.57 (m, 1H), 3.05-3.15 (m, 3H), 3.65-3.71 (m, 2H), 4.20-4.27 (m, 2H), 5.69-5.72 (m, 1H), 6.31-6.38 (m, 1H), 6.55-6.65 (m, 1H)

IR(NaCl): 3474, 2975, 1734, 1649, 1613, 1471, 1417, 1343, 1260, 1191, 1156, 1082, 981, 795, 753 cm$^{-1}$

Example 3a 11.72 g (100 mmol) of 2-(t-butylamino)ethanol (manufactured by Tokyo Chemical Industry Co. Ltd.) was added to 110 mL of dehydrated dichloromethane and 23.07 g (228 mmol) of triethylamine was added thereto. Thereafter, the resultant was cooled in a mixture of dry ice and NaCl to about −15 degrees C. Thereafter, 8.14 g (90 mmol) of acrylic acid chloride (manufactured by Wako Pure Chemical Industries, Ltd.) was diluted with 4 mL of dehydrated dichloromethane and slowly dripped to the resultant followed by stirring at room temperature for three hours. Again, the resultant was cooled in the mixture of dry ice and NaCl to about −15 degrees C. Thereafter, 7.85 g (100 mmol) of acetylchloride was diluted with 4 mL of dehydrated dichloromethane and slowly dripped to the resultant followed by stirring at room temperature for about 1.5 hours. Moreover, after precipitates were removed by filtration, the filtrate was rinsed with water, an aqueous solution of saturated sodium hydrogen carbonate, and an aqueous solution of saturated sodium chloride. Thereafter, subsequent to drying with sodium sulfate, the resultant was condensed under a reduced pressure to obtain oily matter. Moreover, the oily matter was refined by column chromatography filled with 320 g of silicagel C-300 (manufactured by Wako Pure Chemical Industries, Ltd.) using hexane and ethyl acetate as eluate to obtain 0.94 g of pale yellow oily matter of the curable compound represented by the following Chemical structure a6-1 with a yield of about 4.9 percent.

Chemical structure a6-1

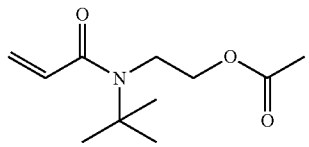

Identification data are as follows.

$^1$H-NMR (CDCl$_3$): δ1.48 (s, 9H), 2.06 (s, 3H), 3.63 (t, 2H), 4.14 (t, 2H), 5.62 (dd, 1H), 6.26 (dd, 1H), 6.63-6.69 (m, 1H)

IR(NaCl): 2966, 1743, 1650, 1612, 1415, 1368, 1234, 1105, 1051, 981, 798 cm$^{-1}$

Example 4a 8.37 g (60 mmol) of methyl ester of sarcosine acid (manufactured by Tokyo Chemical Industry Co. Ltd.) was added to 100 mL of dehydrated dichloromethane and 17.49 g (172 mmol) of triethylamine was added thereto. Thereafter, the resultant was cooled in a mixture of dry ice and NaCl to about −15 degrees C. Thereafter, 6.52 g (72 mmol) of acrylic acid chloride (manufactured by Wako Pure Chemical Industries, Ltd.) was diluted with 4 mL of dehydrated dichloromethane and slowly dripped to the resultant followed by stirring at room temperature for three hours. Moreover, after precipitates were removed by filtration, the filtrate was rinsed with water, an aqueous solution of saturated sodium hydrogen carbonate, and an aqueous solution of saturated sodium chloride. Thereafter, subsequent to drying with sodium sulfate, the resultant was condensed under a reduced pressure to obtain oily matter. Moreover, the oily matter was refined by column chromatography filled with 300 g of silicagel C-300 (manufactured by Wako Pure Chemical Industries, Ltd.) using hexane and ethyl acetate as eluate to obtain 4.69 g of pale yellow oily matter of the curable compound represented by the following Chemical structure d1-1 with a yield of about 0 percent.

Chemical structure d1-1

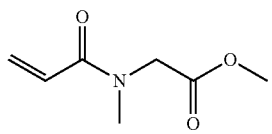

Identification data are as follows.

$^1$H-NMR (CDCl$_3$): δ3.05/3.16 (s, 3H), 3.75/3.78 (s, 3H), 4.13/4.20 (s, 2H), 5.68-5.76 (m, 1H), 6.28-6.44/6.61-6.66 (m, 2H)

IR(NaCl): 3484, 2955, 1748, 1650, 1614, 1482, 1459, 1437, 1420, 1367, 1280, 1212, 1125, 1060, 1010, 981, 940, 890, 847, 797, 709, 555 cm$^{-1}$

Example 5a 12.29 g (80 mmol) of ethyl ester of sarcosine acid (manufactured by Tokyo Chemical Industry Co. Ltd.) was added to 110 mL of dehydrated dichloromethane and 22.34 g (220 mmol) of triethylamine was added thereto. Thereafter, the resultant was cooled in a mixture of dry ice and NaCl to about −15 degrees C. Thereafter, 8.69 g (96 mmol) of acrylic acid chloride (manufactured by Wako Pure Chemical Industries, Ltd.) was diluted with 5 mL of dehydrated dichloromethane and slowly dripped to the resultant followed by stirring at room temperature for three hours.

Moreover, after precipitates were removed by filtration, the filtrate was rinsed with water, an aqueous solution of saturated sodium hydrogen carbonate, and an aqueous solution of saturated sodium chloride. Thereafter, subsequent to drying with sodium sulfate, the resultant was condensed under a reduced pressure to obtain oily matter. Moreover, the oily matter was refined by column chromatography filled with 300 g of silicagel C-300 (manufactured by Wako Pure Chemical Industries, Ltd.) using hexane and ethyl acetate as eluate to obtain 7.58 g of pale yellow oily matter of the curable compound represented by the following Chemical structure d1-2 with a yield of about 55 percent.

Chemical structure d1-2

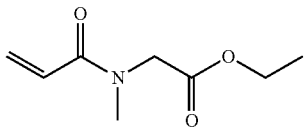

Identification data are as follows.
$^1$H-NMR (CDCl$_3$): δ1.26-1.31 (m, 3H), 3.06/3.16 (s, 3H), 4.11-4.25 (m, 4H), 5.68-5.76 (m, 1H), 6.28-6.44/6.61-6.66 (m, 2H)
IR(NaCl): 3483, 2984, 1745, 1653, 1614, 1477, 1419, 1375, 1280, 1201, 1123, 1032, 980, 797 cm$^{-1}$ Example 6a 9.68 g (70 mmol) of potassium carbonate was added to 31.05 g (70 mmol) of methyhlamine (ca. 7 percent in tetrahydrofuran (THF)) of Tokyo Chemical Industry Co. Ltd. and 15 mL of THF followed by stirring at room temperature. The resultant was dripped to a solution in which 11.60 g (77 mmol) of chloroacetic acid n-butyl of Tokyo Chemical Industry Co. Ltd. was dissolved in 5 mL of THF to cause reaction to obtain reaction liquid. Thereafter, the thus-obtained reaction liquid was filtrated. Thereafter, a solution in which 9.68 g (70 mmol) of potassium carbonate was dissolved in 50 mL of water was added to the thus-obtained filtrate followed by cooling in an ice bath. 6.96 g (77 mmol) of acrylic acid chloride was slowly dripped followed by stirring at room temperature for two hours. Thereafter, using ethylacetate, the resultant was separated into each layer by extraction to sample-split the ethylacetate layer. The thus-obtained ethylacetate layer was rinsed with an aqueous solution of saturated sodium hydrogen carbonate followed by drying with anhydrous sodium sulfate and condensation to obtain 13.3 g of a clear solution.

Moreover, the clear solution was refined by column chromatography filled with 300 g of silicagel C-300 (manufactured by Wako Pure Chemical Industries, Ltd.) using hexane and ethyl acetate as eluate to obtain 5.5 g of clear liquid of the curable compound represented by the following Chemical structure d1-4 with a yield of about 39 percent.

Chemical structure d1-4

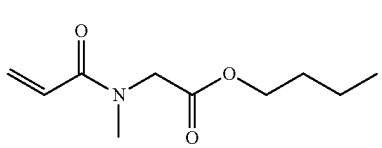

Identification data are as follows.
$^1$H-NMR (CDCl$_3$): δ0.93 (t, 3H), 1.34-1.42 (m, 2H), 1.59-1.66 (m, 2H), 3.06/3.16 (s, 3H), 4.11-4.19 (m, 4H), 5.68-5.76 (m, 1H), 6.28-6.44/6.60-6.66 (m, 2H)

IR(NaCl): 2961, 2936, 2874, 1747, 1655, 1617, 1466, 1418, 1378, 1362, 1308, 1279, 1198, 1122, 1061, 1031, 979, 797 cm$^{-1}$

Example 7a 9.68 g (70 mmol) of potassium carbonate was added to 31.05 g (70 mmol) of methyhlamine (ca. 7 percent in tetrahydrofaran (THF)) of Tokyo Chemical Industry Co. Ltd. and 15 mL of THF followed by stirring at room temperature. The resultant was dripped to a solution in which 10.52 g (77 mmol) of chloroacetic acid isopropyl of Tokyo Chemical Industry Co. Ltd. was dissolved in 5 mL of THF to cause reaction to obtain reaction liquid. Thereafter, the thus-obtained reaction liquid was filtrated. Thereafter, a solution in which 9.68 g (70 mmol) of potassium carbonate was dissolved in 50 mL of water was added to the thus-Obtained filtrate followed by cooling in an ice bath. 6.96 g (77 mmol) of acrylic acid chloride was slowly dripped followed by stirring at room temperature for two hours. Thereafter, using ethylacetate, the resultant was separated into each layer by extraction to sample-split the ethylacetate layer. The thus-obtained ethylacetate layer was rinsed with an aqueous solution of saturated sodium hydrogen carbonate followed by drying with anhydrous sodium sulfate and condensation to obtain 8.4 g of a clear solution.

Moreover, the clear solution was refined by column chromatography filled with 300 g of silicagel C-300 (manufactured by Wako Pure Chemical Industries, Ltd.) using hexane and ethyl acetate as eluate to obtain 3.9 g of clear liquid of the curable compound represented by the following Chemical structure d1-5 with a yield of about 30 percent.

Chemical structure d1-5

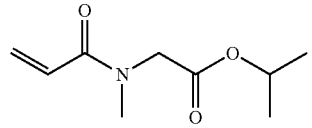

Identification data are as follows.
$^1$H-NMR (CDCl$_3$): δ1.26 (d, 6H), 3.05/3.15 (s, 3H), 4.07/4.16 (s, 2H), 5.04-5.10 (m, 1H), 5.67-5.75 (m, 1H), 6.28-6.44/6.61-6.66 (m, 2H)
IR(NaCl): 2938, 2982, 1741, 1655, 1617, 1467, 1418, 1374, 1279, 1211, 1107, 1060, 980, 957, 900, 837, 797, 726 cm$^{-1}$ Example 8a 5.25 g (88.8 mmol) of n-propylamine of Tokyo Chemical Industry Co. Ltd. was dissolved in 60 mL of ethylacetate and 12.27 g (88.8 mmol) of potassium carbonate was added thereto. Thereafter, a solution in which 10.88 g (88.8 mmol) of ethyl acetate of Tokyo Chemical Industry Co. Ltd. was dissolved in 10 mL of ethylacetate was dripped to the resultant at room temperature followed by stirring for four hours to cause reaction, thereby obtaining reaction liquid. Thereafter, the thus-obtained reaction liquid was filtrated and the precipitated salt due to the filtration was removed. Thereafter, the resultant was condensed to obtain 12.3 g of clear solution. This solution was left at room temperature. As a result, a clear crystal was obtained and rinsed with ethylacetate for drying to obtain 5.8 g of N-propyl sarcosine ethyl ester. This compound was used in the following reaction as was.

10 mL of water was added to 5.8 g (40 mmol) of N-propyl sarcosine ethyl ester and thereafter a solution in which 6.08 g (44 mmol) of potassium carbonate was dissolved in 20 mL of water was added followed by cooling in an ice bath. 3.98 g (44 mmol) of acrylic acid chloride was slowly dripped followed by stirring at room temperature for two hours. Thereafter, using ethylacetate, the resultant was separated into each layer by extraction to sample-split the ethylacetate layer. The thus-obtained ethylacetate layer was rinsed with an aqueous solution of saturated sodium hydrogen carbonate followed by drying with anhydrous sodium sulfate and condensation to obtain 7.0 g of a clear solution.

Moreover, the clear solution was refined by column chromatography filled with 300 g of silicagel C-300 (manufactured by Wako Pure Chemical Industries, Ltd.) using hexane and ethyl acetate as eluate to obtain 4.9 g of clear liquid of the curable compound represented by the following Chemical structure d3-2 with a yield of about 62 percent.

Chemical structure d3-2

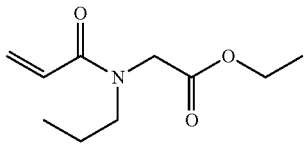

Identification data are as follows.
$^1$H-NMR (CDCl$_3$): δ0.90-0.95 (m, 3H), 1.26-1.30 (m, 3H), 1.56-1.71 (m, 2H), 3.37-3.44 (m, 2H), 4.08/4.12 (s, 2H) 4.18-4.25 (m, 2H), 5.67-5.74 (m, 1H), 6.28-6.42/6.58-6.63 (m, 2H)
IR(NaCl): 2968, 2937, 2877, 1749, 1653, 1616, 1442, 1406, 1374, 1233, 1198, 1185, 1025, 979, 796 cm$^{-1}$ Example 9a 2.95 g (50 mmol) of isopropylamine of Tokyo Chemical Industry Co. Ltd. was dissolved in 50 mL of ethylacetate and 6.91 g (50 mmol) of potassium carbonate was added thereto followed by stirring at room temperature. Thereafter, a solution in which 5.43 g (50 mmol) of methyl acetate of Tokyo Chemical Industry Co. Ltd. was dissolved in 5 mL of ethylacetate was dripped to the resultant at room temperature followed by stirring for two hours to cause reaction, thereby obtaining reaction liquid. Thereafter, the thus-obtained reaction liquid was filtrated and the precipitated salt due to the filtration was removed. Thereafter, a solution in which 6.91 g (50 mmol) of potassium carbonate was dissolved in 50 mL of water was added. After ice bathing, 4.98 g (55 mmol) of acrylic acid chloride was slowly dripped followed by stirring at room temperature for two hours. Thereafter, using ethylacetate, the resultant was separated into each layer by extraction to sample-split the ethylacetate layer. The thus-obtained ethylacetate layer was rinsed with an aqueous solution of saturated sodium hydrogen carbonate followed by drying with anhydrous sodium sulfate and condensation to obtain 9.8 g of a clear solution.

Moreover, the clear solution was refined by column chromatography filled with 300 g of silicagel C-300 (manufactured by Wako Pure Chemical Industries, Ltd.) using hexane and ethyl acetate as eluate to obtain 3.7 g of clear liquid of the curable compound represented by the following Chemical structure d4-1 with a yield of about 40 percent.

Chemical structure d4-1

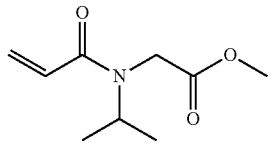

Identification data are as follows.
$^1$H-NMR (CDCl$_3$): δ1.11/1.22 (d, 6H), 3.74/3.77 (s, 3H) 3.99 (s, 2H), 4.26-4.32 (m, 1H) 5.66-5.73 (m, 1H), 6.31-6.35/6.62-6.67 (m, 2H)
IR(NaCl): 2974, 1755, 1645, 1612, 1542, 1446, 1368, 1341, 1205, 1129, 1884, 1062, 985, 797 cm$^{-1}$ Example 10a A solution in which 6.83 g (50 mmol) of isopropyl chloroaceate of Tokyo Chemical Industry Co. Ltd. was diluted with 5 mL of ethylacetate was dripped to a mixture of 2.95 g (50 mmol) of isopropyl amine of Tokyo Chemical Industry Co. Ltd., 50 mL of ethyl acetate, and 6.91 g (50 mmol) of potassium carbonate to cause reaction to obtain a reaction liquid. Thereafter, the thus-obtained reaction liquid was filtrated and the precipitated salt due to the filtration was removed. Thereafter, a solution in which 6.91 g (50 mmol) of potassium carbonate was dissolved in 50 mL of water was added. After ice bathing, 4.98 g (55 mmol) of acrylic acid chloride was slowly dripped followed by stirring at room temperature for two hours. Thereafter, using ethylacetate, the resultant was separated into each layer by extraction to sample-split the ethylacetate layer. The thus-obtained ethylacetate layer was rinsed with an aqueous solution of saturated sodium hydrogen carbonate followed by drying with anhydrous sodium sulfate and condensation to obtain 8.5 g of a clear solution.

Moreover, the clear solution was refined by column chromatography filled with 300 g of silicagel C-300 (manufactured by Wako Pure Chemical Industries, Ltd.) using hexane and ethyl acetate as eluate to obtain 1.3 g of clear liquid of the curable compound represented by the following Chemical structure d4-5 with a yield of about 12 percent.

Chemical structure d4-5

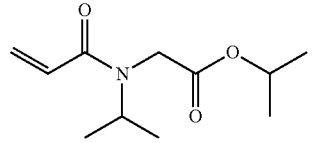

Identification data are as follows.
$^1$H-NMR (CDCl$_3$): δ1.11/1.21 (d, 6H), 1.25 (d, 6H), 3.95 (s, 2H), 4.28/4.93 (m, 1H), 5.05 (m, 1H), 5.65-5.71 (m, 1H), 6.29-6.34/6.61-6.67 (m, 2H)
IR(NaCl): 2981, 2939, 2879, 1746, 1650, 1614, 1465, 1443, 1373, 1340, 1286, 1256, 1202, 1146, 1108, 1084, 1060, 1010, 977, 958, 900, 836, 796, 757, 718 cm$^{-1}$ Example 11a 9.55 g (88 mmol) of methyl chloroaceate of Tokyo Chemical Industry Co. Ltd. was dripped to a mixture of 8.10 g (80 mmol) of n-hexylamine of Tokyo Chemical Industry Co. Ltd., 55 mL of ethyl acetate, and 11.3 g (81.8 mmol) of potassium carbonate to cause reaction to obtain a reaction liquid. Thereafter, the thus-obtained reaction liquid was filtrated and the precipitated salt due to the filtration was removed. Thereafter, a solution in which 11.05 g (80 mmol) of potassium carbonate was dissolved in 80 mL of water was added. After ice bathing, 8.0 g (88 mmol) of acrylic acid chloride was slowly dripped followed by stirring at room temperature for two hours. Thereafter, using ethylacetate, the resultant was separated into each layer by extraction to sample-split the ethylacetate layer.

The thus-obtained ethylacetate layer was rinsed with an aqueous solution of saturated sodium hydrogen carbonate followed by drying with anhydrous sodium sulfate and condensation to obtain 16.1 g of a clear solution.

Moreover, the clear solution was refined by column chromatography filled with 300 g of silicagel C-300 (manufactured by Wako Pure Chemical Industries, Ltd.) using hexane and ethyl acetate as eluate to obtain 3.5 g of clear liquid of the curable compound represented by the following Chemical structure d6-1 with a yield of about 19 percent.

Chemical structure d6-1

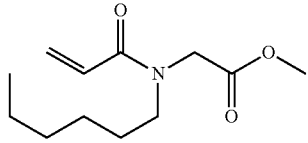

Identification data are as follows $^1$H-NMR (CDCl$_3$): δ0.89 (t, 3H), 1.26-1.33 (m, 6H), 1.58-1.61 (m, 2H), 3.40/3.44 (t, 2H), 3.74/3.77 (s, 3H), 4.10/4.13 (s, 2H), 5.67-5.75 (m, 1H), 6.29-6.42/6.57-6.62 (m, 2H)

IR(NaCl): 2955, 2931, 2858, 1753, 1653, 1616, 1439, 1406, 1373, 1250, 1206, 1178, 1138, 1063, 979, 796 cm$^{-1}$

Example 12a

A solution in which 7.53 g (50 mmol) of n-butyl chloroacetate of Tokyo Chemical Industry Co. Ltd. was diluted with 5 mL of ethylacetate was dripped to a mixture of 5.06 g (50 mmol) of n-hexyl amine of Tokyo Chemical Industry Co. Ltd., 50 mL of ethyl acetate, and 6.91 g (50 mmol) of potassium carbonate to cause reaction to obtain a reaction liquid. Thereafter, the thus-obtained reaction liquid was filtrated and the precipitated salt due to the filtration was removed. Thereafter, a solution in which 6.91 g (50 mmol) of potassium carbonate was dissolved in 50 mL of water was added. After ice bathing, 4.98 g (55 mmol) of acrylic acid chloride was slowly dripped followed by stirring at room temperature for two hours. Thereafter, using ethylacetate, the resultant was separated into each layer by extraction to sample-split the ethylacetate layer. The thus-obtained ethylacetate layer was rinsed with an aqueous solution of saturated sodium hydrogen carbonate followed by drying with anhydrous sodium sulfate and condensation to obtain 13.4 g of a clear solution.

Moreover, the clear solution was refined by column chromatography filled with 300 g of silicagel C-300 (manufactured by Wako Pure Chemical Industries, Ltd.) using hexane and ethyl acetate as eluate to obtain 5.8 g of clear liquid of the curable compound represented by the following Chemical structure d6-4 with a yield of about 43 percent Chemical structure d6-4

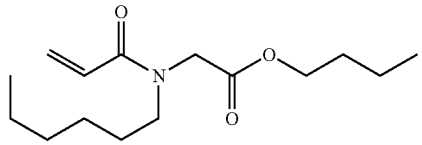

Identification data are as follows.

$^1$H-NMR (CDCl$_3$): δ0.88-1.62 (m, 18H), 3.40/3.44 (t, 2H), 4.05/4.08 (s, 2H), 4.14 (t, 2H), 5.66-5.74 (m, 1H), 6.29-6.41/6.56-6.62 (m, 2H)

IR(NaCl): 2958, 2931, 2882, 2860, 1748, 1652, 1614, 1539, 1456, 1377, 1196, 1137, 1064, 1022, 977, 795, 725 cm$^{-1}$

Example 13a 6.19 g (60 mmol) of N-methyl-DL-alamine (60 mmol) of Combi-Blocks Inc. was mixed with 40 mL of methanol to obtain a slurry. The slurry was cooled in ice bath and thereafter, 14.28 g (120 mmol) of thionyl chloride was slowly dripped to cause reaction to obtain a reaction liquid. The reaction liquid changed to a clear solution in the middle of the dripping followed by stirring at room temperature all night. Thereafter, the thus-obtained reaction liquid was condensed to obtain 8.3 g of methylester chloric acid salt of N-methyl-DL-alanine as a clear and viscous liquid. The thus-obtained methylester chloric acid salt of N-methyl-DL-alanine was used as was in the next reaction.

8.3 g (54 mmol) of methlester chloric acid salt of N-methyl-DL-alanine was dissolved in 20 mL of water and a solution in which 11.94 g (86.5 mmol) of potassium carbonate was dissolved in 20 mL of water was added followed by stirring at room temperature for one hour. After cooling in ice bath, 5.38 g (59.4 mmol) of acrylic acid chloride was slowly dripped followed by stirring at room temperature for two hours. Thereafter, using ethylacetate, the resultant was separated into each layer by extraction to sample-split the ethylacetate layer. The thus-obtained ethyl acetate layer was rinsed with saturated salt solution and condensed to obtain 6.0 g of pale yellow liquid.

Moreover, the pale yellow liquid was refined by column chromatography filled with 300 g of silicagel C-300 (manufactured by Wako Pure Chemical Industries, Ltd.) using hexane and ethyl acetate as eluate to obtain 4.1 g of clear liquid of the curable compound represented by the following Chemical structure g1-1 with a yield of about 44 percent.

Chemical structure g1-1

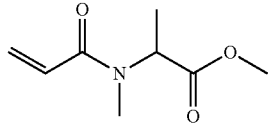

Identification data are as follows.

$^1$H-NMR (CDCl$_3$): δ1.43/1.49 (d, 3H), 2.91/3.03 (s, 3H), 3.72/3.75 (s, 3H), 4.68/5.29 (q, 1H), 5.68-5.76 (m, 1H), 6.22-6.39 (m, 1H), 6.49-6.63 (m, 1H)

IR(NaCl): 2989, 2952, 1742, 1651, 1614, 1446, 1416, 1332, 1281, 1211, 1096, 981, 845, 796 cm$^{-1}$

Example 14a 6.19 g (60 mmol) of N-methyl-DL-alanine (60 mmol) of Combi-Blocks Inc. was mixed with 40 mL of ethanol to obtain a slurry. The slurry was cooled in ice bath and thereafter, 14.28 g (120 mmol) of thionyl chloride was slowly dripped to cause reaction to obtain a reaction liquid. The reaction liquid was changed to a clear solution in the middle of dripping and thereafter white solid precipitated to become a slurry. Keeping the slurry state, it was stirred at room temperature all night. As a result, the white solid was dissolved to obtain a clear reaction solution. The thus-obtained reaction solution was condensed to obtain 10.3 g of ethylester chloric acid salt of N-methyl-DL-alanine as a clear and viscous liquid. The thus-obtained ethylester chloric acid salt of N-methyl-DL-alanine was used as was in the next reaction.

Thereafter, 10.3 g (61.4 mmol) of ethylester chloric acid salt of N-methyl-DL-alanine was dissolved in 12 mL of water and a solution in which 15.28 g (110.6 mmol) of potassium carbonate was dissolved in 25 mL of water was added followed by stirring at room temperature for one hour. After cooling in an ice bath, 6.11 g (67.5 mmol) of acrylic acid chloride was slowly dripped followed by stirring at room temperature for two hours. Thereafter, using ethylacetate, the resultant was separated into each layer by extraction to sample-split the ethylacetate layer. The thus-obtained ethyl acetate layer was rinsed with saturated salt solution and condensed to obtain 11.5 g of pale yellow liquid.

Moreover, the pale yellow liquid was refined by column chromatography filled with 300 g of silicagel C-300 (manufactured by Wako Pure Chemical Industries, Ltd.) using hexane and ethyl acetate as eluate to obtain 8.1 g of clear liquid of the curable compound represented by the following Chemical structure g1-2 with a yield of about 71 percent.

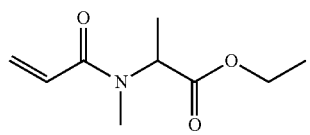

Chemical structure g1-2

Identification data are as follows.
$^1$H-NMR (CDCl$_3$): δ1.27 (t, 3H), 1.43/1.48 (d, 3H), 2.91/3.03 (s, 3H), 4.14-4.22 (m, 2H), 4.66/5.29 (q, 1H), 5.67-5.75 (m, 1H), 6.22-6.38 (m, 1H), 6.50-6.63 (m, 1H)
IR(NaCl): 2984, 2941, 1738, 1651, 1613, 1447, 1416, 1378, 1329, 1281, 1203, 1094, 1023, 981, 859, 796 cm$^{-1}$

Example 15a 6.19 g (60 mmol) of N-methyl-DL-alanine (60 mmol) of Combi-Blocks Inc. was mixed with 40 mL of isopropyl alcohol to obtain a slurry. The slurry was cooled in ice bath and thereafter, 14.28 g (120 mmol) of thionyl chloride was slowly dripped to cause reaction to obtain a reaction liquid. The reaction liquid was changed to a clear solution in the middle of dripping and thereafter white solid precipitated to become a slurry. The slurry was stirred at room temperature all night but the white solid was not dissolved and the slurry state was kept. The thus-obtained reaction liquid was condensed to obtain 10.0 g of isopropylester chloric acid salt of N-methyl-DL-alanine as a clear solid. The thus-obtained isopropyl ester chloric acid salt of N-methyl-DL-alanine was used as was in the next reaction.

Thereafter, 10.0 g (55 mmol) of isopropyl ester chloric acid salt of N-methyl-DL-alanine was dissolved in 12 mL of water and a solution in which 13.69 g (99.1 mmol) of potassium carbonate was dissolved in 25 mL of water was added followed by stirring at room temperature for one hour. After cooling in an ice bath, 5.48 g (60.6 mmol) of acrylic acid chloride was slowly dripped followed by stirring at room temperature for two hours. Thereafter, using ethylacetate, the resultant was separated into each layer by extraction to sample-split the ethylacetate layer. The thus-obtained ethyl acetate layer was rinsed with saturated salt solution and condensed to obtain 5.5 g of light brown liquid.

Moreover, the light brown liquid was refined by column chromatography filled with 300 g of silicagel C-300 (manufactured by Wako Pure Chemical Industries, Ltd.) using hexane and ethyl acetate as eluate to obtain 1.9 g of clear liquid of the curable compound represented by the following Chemical structure g1-5 with a yield of about 17 percent.

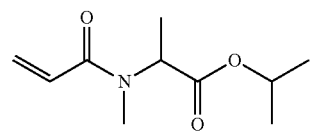

Chemical structure g1-5

Identification data are as follows.
$^1$H-NMR (CDCl$_3$): δ1.25 (d, 6H) 1.41/1.46 (d, 3H), 2.90/3.02 (s, 3H) 4.99-5.07 (m, 1H) 4.62/5.27 (q, 1H), 5.67-5.75 (m, 1H), 6.22-6.38 (m, 1H), 6.50-6.63 (m, 1H)
IR(NaCl): 2982, 2940, 1735, 1652, 1614, 1466, 1453, 1415, 1375, 1325, 1281, 1207, 1109, 1018, 981, 910, 865, 828, 796 cm$^{-1}$

Comparative Example 1a

N,N-diethylacrylamide (manufactured by KJ Chemicals Co oration) represented by the following Chemical structure 1 was used as the compound of Comparative Example 1

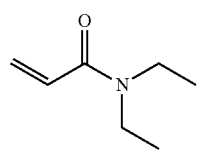

Chemical structure 1

Comparative Example 2a

According to the method described in Example 1 of Japanese Unexamined Patent Application Publication No. 2015-13980, acrylamide represented by the following Chemical structure 2 was synthesized and used as the compound of Comparative Example 2.

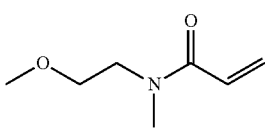

Chemical structure 2

Comparative Example 3a

According to the method described in Example 5 of Japanese Unexamined Patent Application Publication No. 2015-13980, acrylamide represented by the following Chemical structure 3 was synthesized and used as the compound of Comparative Example 3a.

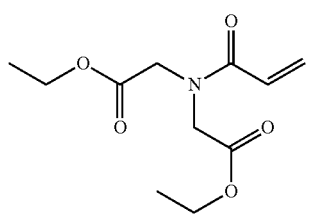

Chemical structure 3

The thus-obtained curable compound was evaluated regarding viscosity, odor, and safeness in the following manner. The results are shown in Table 1.

Measuring of Viscosity

Viscosity of the thus-obtained curable compound was measured by a cone plate type rotatory viscometer (VISCOMETER TVE-22L, manufactured by TOKI SANGYO CO., LTD.) using a cone rotor (1°34'×R24) at a number of rotation of 50 rpm and at 25 degrees C. of hemathermal circulating water.

Evaluation on Odor

The odor of the thus-obtained curable compound was checked according to the following procedures of (1) to (3) and evaluated based on the following evaluation criteria.
(1) About 100 mg (0.1 g) of each compound was weighed and loaded in a sample bin (50 mL glass bin) and the lid thereof was closed.
(2) Left about 30 minutes under room temperature condition.
(3) The odor was smelt by approaching nose to the sample bin (glass bin) when the lid was opened.

Evaluation Criteria

A: no odor or not uncomfortable if any
B: uncomfortable with peculiar odor
C: Very uncomfortable with peculiar odor Evaluation on Safeness The curable compounds of Example 1a, Example 4a, Comparative Example 1a, and Comparative Example 2a were subject to the limiting test based on Acute Oral Toxicity Test (OECD TG423) according to Acute Toxic Class Method in the following manner to evaluate safeness.

Limiting Test Based on Acute Oral Toxicity Test

Animals Used

Regarding the curable compound of the present disclosure as test article, 24 female rats of Slc: Wistar/ST series of 5 week old as animal used were ordered for Japan SLC, Inc. The animals were habituated for one week. No abnormalities were found in all of the rats (animals used) during the habituation period.

Based on the body weights measured two days before the initiation of administration, they were categorized into four groups (six rats per group) by the body weight stratified random sampling method so that the body weight of each individual was within ±20% of the average body weight of all of the individuals. The individuals not classified into the groups were excluded from the test.

The animals used were individually identified by application of oil ink to their tales throughout the test period. Also their cages were labeled for identification.

Housing Environment

Throughout the housing period including the quarantine habituation period, the animals used were housed in an animal room with a barrier system, which was set as follows: temperature: 19 to 25 degrees C., relative humidity: 40 to 70 percent, frequency of ventilation: 10 to 15 times per hour, 12 hour-interval lighting cycle (lighted from 7:00 to 19:00).

The housing cages used were made of polycarbonate. Six rats were housed in one cage.

The animals used were given solid feed for mouse and rat (LaboMRStock, manufactured by Noun Corporation.) ad libitum.

The housing cage and the bedding were replaced with new ones at the time of the grouping and the removal of the auricular lymph node (i.e., the time when the animals were transferred from the housing room), and the water-supply bottle and rack were replaced with new ones at the time of the grouping.

Test Method

Group Composition

The group composition used in the limiting test are as follows.

First group, Example 1a: Testing article: curable compound represented by the chemical structure a1-1, Amount of administration: 2,000 mg/kg weight of body, number of animals used: six Second group, Example 4a: Testing article: curable compound represented by the chemical structure d1-1, Amount of administration: 2,000 mg/kg weight of body, number of animals used: six Third group, Comparative Example 1a: Testing article: N,N-diethylacrylamide represented by the chemical structure (1), Amount of administration: 2,000 mg/kg weight of body, number of animals used: six Fourth group, Comparative Example 2a: Testing article: Acrylamide represented by the chemical structure (2), Amount of administration: 2,000 mg/kg weight of body, number of animals used: six Preparation of Testing Article 100 mg of the testing article was weighed using a measuring flask and water was added as solvent to make 1 mL in total. The obtained preparation liquid had a preparation concentration of 100 mg/mL. The preparation liquid of the testing article was prepared on the day of administration.

Administration

The animals used were on fasting except for water for 17 hours before administration. The mass was measured after the fasting and the testing article was provided by gavage administration one time using a gastric tube. After the administration, no food was given for another three to four hours.

The administration was on one dose of 2,000 mg/kg weight of body and six animals were used per testing article.

Observation

All the animals used for the test were observed at least once per day for 14 days from the initiation of the administration. Note that the observation was counted from the day of the initiation of administration being regarded as Day 1.

The number of animals who died during the test period was counted.

TABLE 1

| | Curable compounds | Evaluation results | | |
|---|---|---|---|---|
| | | Viscosity (25 degrees C., mPA·s) | Odor (no odor) | Safeness (number of dead) |
| Example 1a | a1-1 | 8.4 | A | 3 |
| Example 2a | a1-4 | 9.5 | A | — |
| Example 3a | a6-1 | 16.4 | A | — |
| Example 4a | d1-1 | 12.3 | A | 0 |
| Example 5a | d1-2 | 11.4 | A | — |
| Example 6a | d1-4 | 11.9 | A | — |
| Example 7a | d1-5 | 14.1 | A | — |
| Example 8a | d3-2 | 20.4 | A | — |
| Example 9a | d4-1 | 25.4 | A | — |
| Example 10a | d4-5 | 22.1 | A | — |
| Example 11a | d6-1 | 29.9 | A | — |
| Example 12a | d6-4 | 23.7 | A | — |
| Example 13a | g1-1 | 8.9 | A | — |
| Example 14a | g1-2 | 6.9 | A | — |
| Example 15a | g1-5 | 6.8 | A | — |
| Comparative Example 1a | N,N-diethyl-acrylamide | 2.6 | C | 6 |
| Comparative Example 2a | Acrylamide represented by Chemical structure 2 | 2.4 | A | 6 |
| Comparative Example 3a | Acrylamide represented by Chemical structure 3 | 69.2 | A | — |

As seen in rs in Table 1, viscosity of the curable compounds of Examples 1a to 15a was low. Also, the curable compounds produced less odor and handling thereof was easy.

Examples 1b to 15b and Comparative Examples 1b to 3b

Preparation of Curable Composition 950 mg of each curable compound of Examples 1a to 15a and Comparative Examples 1a to 3a and 50 mg of a polymerization initiator (IRGACURE 907, 2-methyl-1-[4-(methylthio)phenyl]-2-morpholinopropan I-one, manufactured by BASF) were respectively mixed using a magnetic stirrer to prepare the curable compositions of Examples 1b to 15b and Comparative Examples 1b to 3b.

Polymerization property and curability of each curable composition of Examples 1b to 15b and Comparative Examples 1b to 3b were evaluated in the following manner. The results are shown in Table 2.

Evaluation on Polymerization Property

Polymerization property of each curable composition was evaluated using a measuring device in which a scanning differential thermometer (DSC-7020, manufactured by Seiko Instruments Inc.) was combined with a spot light source (LA-410UV, manufactured by HAYASHI WATCH-WORKS).

Specifically, the amount of heat generation was measured twice for one sample when the curable compound was irradiated with ultraviolet rays having a wavelength of 365 nm in an amount of 200 mW/cm² for a period of time long enough to complete the polymerization.

The amount of generation heat for the first measuring included the amount of generation heat caused by ultraviolet rays as well as the amount of generation heat ascribable to the polymerization of the curable compound. The sample completed with the polymerization for the first measuring was irradiated again with the ultraviolet rays in the same conditions to measure the amount of generation heat other than the amount of generation heat ascribable to the polymerization of the curable compound. Based on the difference of the amount of generation heat between the first time and the second time, the amount of generation heat ascribable to the polymerization of the curable compound was calculated. The time Ti (seconds) from the start of irradiation of the ultraviolet rays until the amount of generation heat reached the maximum was used as an index of comparison of the speed of the polymerization.

Evaluation on Curability

Curability of each curable composition was evaluated using a viscoelasticity measuring device (MCR302, manufactured by Anton-Parr Gmbh) and optional devices of UV curing measuring cell and LED light source (LIGHTNING-CURE LC-L1, manufactured by Hamamatsu Photonics K.K.).

Specifically, the sample was pinched in the gap of 10 μm using a cone plate having a diameter of 20 mm and thereafter irradiated with ultraviolet rays having a wavelength of 365 nm to measure the change of viscoelasticity until modulus of elasticity saturated. The maximum value of the saturated storage elastic modulus was obtained from the measuring results and determined as an index of the degree of curing.

In addition, energy of the ultraviolet rays emitted until the storage elastic modulus saturated, viz., curing energy was calculated from the product of the strength of ultraviolet rays (50 mW/cm²) and the time (second) of irradiation of the ultraviolet rays.

TABLE 2

| | Curable compounds | Evaluation results | | |
|---|---|---|---|---|
| | | Polymerization property $T_1$ (seconds) | Curability | |
| | | | Saturated modulus of elasticity (Pa) | Curing energy (mJ/cm²) |
| Example 1b | a1-1 | 6.0 | $3.4 \times 10^5$ | 225 |
| Example 2b | a1-4 | 4.8 | $3.0 \times 10^5$ | 255 |
| Example 3b | a6-1 | 4.4 | $5.0 \times 10^5$ | 360 |
| Example 4b | d1-1 | 6.6 | $5.2 \times 10^5$ | 318 |
| Example 5b | d1-2 | 6.5 | $4.0 \times 10^5$ | 293 |
| Example 6b | d1-4 | 3.0 | $1.0 \times 10^6$ | 110 |
| Example 7b | d1-5 | 3.0 | $5.0 \times 10^5$ | 100 |
| Example 8b | d3-2 | 2.4 | $4.6 \times 10^5$ | 108 |
| Example 9b | d4-1 | 3.6 | $5.2 \times 10^5$ | 93 |
| Example 10b | d4-5 | 3.6 | $1.4 \times 10^6$ | 115 |
| Example 11b | d6-1 | 3.0 | $3.9 \times 10^5$ | 100 |
| Example 12b | d6-4 | 3.0 | $1.3 \times 10^4$ | 165 |
| Example 13b | g1-1 | 3.6 | $1.0 \times 10^6$ | 110 |
| Example 14b | g1-2 | 3.6 | $4.7 \times 10^5$ | 140 |
| Example 15b | g1-5 | 4.8 | $8.0 \times 10^5$ | 165 |
| Comparative Example 1b | N,N-diethyl-acrylamide | 4.8 | $1.0 \times 10^5$ | 208 |
| Comparative Example 2b | Acrylamide represented by Chemical structure 2 | 5.4 | $1.0 \times 10^5$ | 421 |
| Comparative Example 3b | Acrylamide represented by Chemical structure 3 | 5.4 | $1.0 \times 10^5$ | 232 |

As seen in the results shown in Table 2, the curable compositions of Examples 1b to 15b using the curable compounds of Examples 1a to 15a were found to strike a balance between polymerization property and curability. This mechanism is thought to be realized because low viscosity was obtained due to the tertiary acrylamide structure having no cyclic structure and volatility was reduced by the ester structure introduced in the molecule so that the reduction of odor and the low viscosity were well balanced. In addition, due to the ester structure, an extremely well-balanced curable composition is provided which has excellent reactivity and curability with reduced odor, safeness, and low viscosity.

Examples 1c to 15c

Preparation of Black Ink 100 parts of the curable compounds of Examples 1a to 15a, 10 parts of polymerization initiator (IRGACURE 907, manufactured by BASF Japan), and 3 parts of carbon black (MICROLITH Black C-K, manufactured by BASF JAPAN) were mixed to obtain black ink of Examples 1c to 15c, respectively.

Example 1d to 15d

Preparation of Blue Ink 100 parts of the curable compounds of Examples 1a to 15a, 10 parts of polymerization initiator (IRGACURE 907, manufactured by BASF Japan) and 3 parts of blue pigment (MICROLITH Blue 4G-K, manufactured by BASF JAPAN) were mixed to obtain black ink of Examples 1d to 15d, respectively.

Evaluation 1 on Curability of Ink

Each ink of Examples 1c to 15c and Examples 1d to 15d was discharged onto a glass slide using an inkjet recording device (Manufactured by Ricoh Company Ltd., with heads of GEN4 manufactured by Ricoh Industry Company, Ltd.) and irradiated with ultraviolet rays having a wavelength of 365 nm in an amount of 200 mW/cm$^3$ to cure using an UV irradiator (LH6, manufactured by Heraeus K.K.).

As a result, each ink was discharged by inkjet method without a problem and the ink image was sufficiently cured.

In addition, each ink substantially corresponds to articles using each curable composition of Examples 1b to 1b. Just to be safe, polymerization and curability thereof were measured in the same manner as in the case of each curable composition and found to be excellent as well as the curable compositions of Examples 1b to 15b.

Evaluation 2 on Curability of Ink

The tip of a dip pen was dipped in each ink of Examples 1c to 15c and Examples 1d to 15d and texts were written on PET film and plain paper with the dip pen. Thereafter, the texts were irradiated with ultraviolet rays having a wavelength of 365 nm in an amount of 200 mW/cm$^3$ to cure using an UV irradiator (LH6, manufactured by Heraeus K.K.).

As a result, the ink image (text) was found to be sufficiently cured.

Embodiments of the present disclosure are, for example, as follows.

1. A curable composition includes an acrylamide compound represented by the following Chemical formula 1:

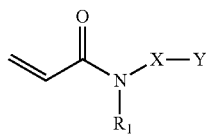

Chemical formula 1

In the Chemical formula 1, $R_1$ represents an alkyl group having 1 to 6 carbon atoms. X represents an alkylene group having 1 to 6 carbon atoms and Y is represents the following Chemical formula 2 or the following Chemical formula 3.

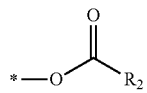

Chemical formula 2

In the Chemical formula 2, $R_2$ represents an alkyl group having 1 to 10 carbon atoms and * represent a band site with X.

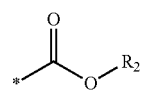

Chemical formula 3

In the Chemical formula 3, $R_2$ represents an alkyl group having 1 to 10 carbon atoms and * represents a bond site with X.

2. The curable composition according to 1 mentioned above, wherein the acrylamide compound represented by the Chemical Formula 1 is represented by the following Chemical Formula 4,

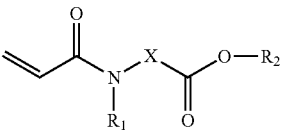

Chemical formula 4

In the Chemical formula 4, $R_1$ represents alkyl group having 1 to 6 carbon atoms, X represents an alkylene group having 1 to 3 carbon atoms, and $R_2$ represents an alkyl group having 1 to 4 carbon atoms.

3. The curable composition according to 2 mentioned above, wherein, in the Chemical formula 4, $R_1$ represents an alkyl group having 1 to 3 carbon atoms and $R_2$ represents an alkyl group having 1 to 3 carbon atoms.

4. The curable composition according to 2 or 3 mentioned above, wherein, in the Chemical formula 4, X represents a methylene group or a methylmethylene group.

5. The curable composition according to any one of 2 to 4, wherein the acrylamide compound represented by the Chemical formula 4 is at least one member selected from the group consisting of a compound represented by the following chemical stricture d1-1, a compound represented by the following chemical structure d1-2, a compound represented by the following chemical structure g1-1, a compound represented by the following chemical structure g1-2, and a compound represented by the following chemical structure 1-5.

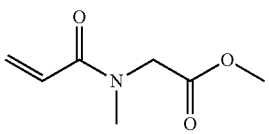

Chemical structure d1-1

Chemical structure d1-2

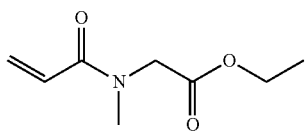

Chemical structure g1-1

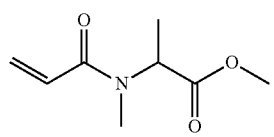

Chemical structure g1-2

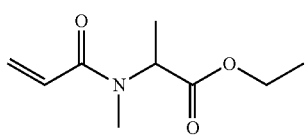

Chemical structure g1-5

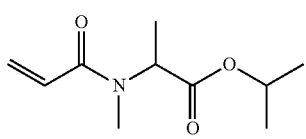

6. The curable composition according to 1 mentioned above, wherein the acrylamide compound represented by the Chemical Formula 1 is represented by the following Chemical structure a1-1, Chemical structure a1-1

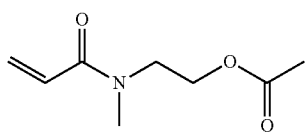

7. The curable composition according to 1 mentioned above, wherein the acrylamide compound represented by the Chemical Formula 1 is represented by the following Chemical structure a1-4, Chemical structure a1-4

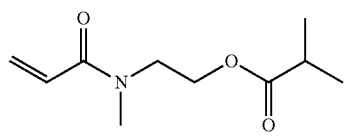

8. The curable composition according to 1 mentioned above, wherein the acrylamide compound represented by the Chemical Formula 1 is represented by the following Chemical structure a6-1, Chemical structure a6-1

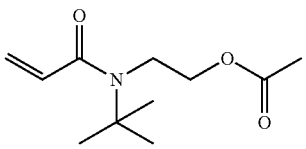

9. A curable ink includes the curable composition of any one of 1 to 8 mentioned above.

10. A curable ink according to 9 mentioned above for inkjet.

11. An accommodating container accommodates at least one of the curable composition of any one of 1 to 8 mentioned above and the curable ink of 9 or 10 mentioned above.

12. An image forming device of two-dimensional images or three-dimensional images includes a accommodating container accommodates at least one of the curable composition of any one of 1 to 8 mentioned above and the curable ink of 9 or 10 mentioned above and an application device to apply energy.

13. An image forming method includes applying energy to at least one of the curable composition of any one of 1 to 8 mentioned above and the curable ink of 9 or 10 mentioned above to form a two-dimensional image or a three-dimensional image.

14. Cured matter formed using at least one of the curable composition of any one of 1 to 8 mentioned above and the curable ink of 9 or 10 mentioned above.

15. A decorated object having a substrate having a surface decorated with the cured matter of 14 mentioned above.

16. A curable compound being an acrylamide compound represented by the following Chemical formula 1.

Chemical formula 1

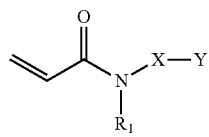

In the Chemical formula 1, $R_1$ represents an alkyl group having 1 to 6 carbon atoms. X represents an alkylene group having 1 to 6 carbon atoms, and Y represents the following Chemical formula 2 or the following Chemical formula 3.

Chemical formula 2

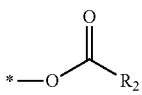

In the Chemical formula 2, $R_2$ represents an alkyl group having 1 to 10 carbon atoms and * represents a bond site with X.

Chemical formula 3

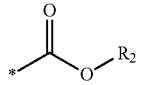

In the Chemical formula 3, $R_2$ represents an alkyl group having 1 to 10 carbon atoms and * represent a bond site with X.

17. The curable composition according to 16 mentioned above, wherein the acrylamide compound represented by the Chemical Formula 1 is represented by the following Chemical Formula 4, Chemical formula 4

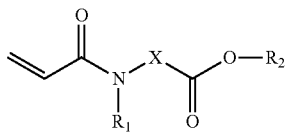

In the Chemical formula 4, $R_1$ represents a alkyl group having 1 to 6 carbon atoms. X represents an alkylene group having 1 to 3 carbon atoms, and $R_2$ represents an alkyl group having 1 to 4 carbon atoms.

18. The curable composition according to 17 mentioned above, wherein, in the Chemical formula 4, $R_1$ represents an alkyl group having 1 to 3 carbon atoms and $R_2$ represents an alkyl group having 1 to 3 carbon atoms.

19. The curable composition according to 17 or 18 mentioned above, wherein, in the Chemical formula 4, X represents methylene group or methylmethylene group.

20. The curable compound according to 19 mentioned above, wherein the acrylamide compound represented by the Chemical formula 4 is at least one member selected from the group consisting of a compound represented by the following chemical structure d1-1, a compound represented by the following chemical structure d1-2, a compound represented by the following chemical structure g1-1, a compound represented by the following chemical structure g1-2, and a compound represented by the following chemical structure 1-3.

Chemical structure d1-1

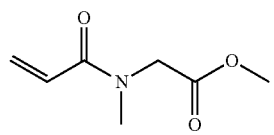

Chemical structure d1-2

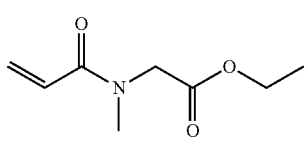

Chemical structure g1-1

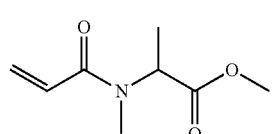

Chemical structure g1-2

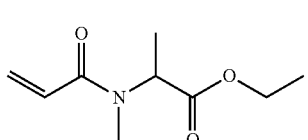

-continued

Chemical structure g1-5

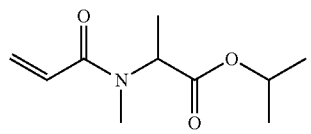

21. The curable composition according to 16 mentioned above, wherein the acrylamide compound represented by the Chemical Formula 1 is represented by the following Chemical structure a1-1, Chemical structure a1-1

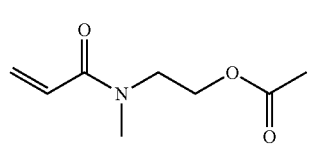

22. The curable composition according to 16 mentioned above, wherein the acrylamide compound represented by the Chemical Formula 1 is represented by the following Chemical structure a1-4, Chemical structure a1-4

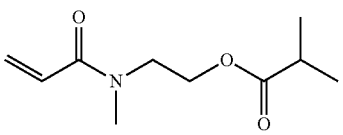

23. The curable composition according to 16 mentioned above, wherein the acrylamide compound represented by the Chemical Formula 1 is represented by the following Chemical structure a6-1, Chemical structure a6-1

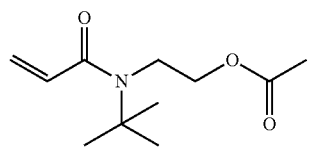

According to the present disclosure, a curable composition is provided which produces less odor and has excellent polymerization property, curability, and safeness.

Having now fully described embodiments of the present invention, it will be apparent to one of ordinary skill in the art that many change and modifications can be made thereto without departing from the spirit and scope of embodiments of the invention as set forth herein.

What is claimed is:

1. A curable composition comprising a coloring agent and an acrylamide compound of chemical structure d1-1 or of chemical structure d1-2

Chemical structure d1-1

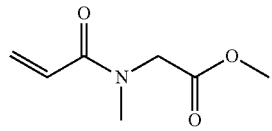

Chemical structure d1-2

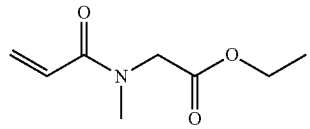

2. A curable ink comprising:
the curable composition of claim 1.

3. The curable ink according to claim 2, wherein the curable ink is used in inkjet printing.

4. An accommodating container comprising:
the curable composition of claim 1 and a curable ink.

5. The curable composition according to claim 1, wherein the acrylamide compound is of chemical structure d1-1.

6. The curable composition according to claim 1, wherein the acrylamide compound is of chemical structure d1-2.

* * * * *